United States Patent
Zheng et al.

(10) Patent No.: US 9,730,672 B2
(45) Date of Patent: Aug. 15, 2017

(54) SYSTEM AND METHOD FOR DETECTING CRITICAL STRUCTURES USING ULTRASOUND

(71) Applicant: Covidien LP, Mansfield, MA (US)

(72) Inventors: Peng Zheng, Longmont, CO (US); Christopher A. Valentine, Boulder, CO (US); Christopher T. Rusin, Golden, CO (US); Kathy E. Rooks, Longmont, CO (US); Benjamin M. Corum, Boulder, CO (US); Sally D. Jandrall, Evergreen, CO (US); Kristin D. Johnson, Louisville, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/194,723

(22) Filed: Jun. 28, 2016

(65) Prior Publication Data
US 2016/0302764 A1    Oct. 20, 2016

Related U.S. Application Data

(63) Continuation of application No. 13/839,562, filed on Mar. 15, 2013, now Pat. No. 9,375,196.
(Continued)

(51) Int. Cl.
A61B 8/12        (2006.01)
A61B 8/00        (2006.01)
(Continued)

(52) U.S. Cl.
CPC ............. *A61B 8/12* (2013.01); *A61B 1/3132* (2013.01); *A61B 8/085* (2013.01); *A61B 8/0891* (2013.01);
(Continued)

(58) Field of Classification Search
CPC ..... A61B 8/4254; A61B 8/085; A61B 8/0891; A61B 8/12; A61B 8/4245; A61B 8/488; A61B 8/445; A61B 8/5223; A61B 8/461; A61B 8/486; A61B 8/5215; A61B 1/3132; A61B 18/1482
See application file for complete search history.

(56) References Cited

U.S. PATENT DOCUMENTS 5,957,849 A    9/1999    Munro
5,991,697 A    11/1999   Nelson et al.
(Continued)

FOREIGN PATENT DOCUMENTS

WO    2008017051 A2    2/2008
WO    2012066446 A1    5/2012

OTHER PUBLICATIONS

European Search Report dated Oct. 23, 2013 for EP 13 17 6292.

*Primary Examiner* — Bo J Peng

(57) ABSTRACT

A system and method of ultrasound imaging, the system including a laparoscopic surgical instrument including at least one ultrasound transducer, and a processor adapted to receive acoustic data from the ultrasound transducer and process the acoustic data from the ultrasound transducer to produce a graphical representation of the acoustic data, the graphical representation depicting echoic attributes of tissue substantially axially aligned with a transmission path of the at least one ultrasound transducer, and the distance of at least one tissue type having different echoic attributes from surrounding tissue form a distal tip of the laparoscopic surgical instrument.

20 Claims, 21 Drawing Sheets

Related U.S. Application Data

(60) Provisional application No. 61/670,713, filed on Jul. 12, 2012.

(51) Int. Cl.
 *A61B 1/313* (2006.01)
 *A61B 8/08* (2006.01)
 *A61B 18/14* (2006.01)

(52) U.S. Cl.
 CPC .......... *A61B 8/4245* (2013.01); *A61B 8/4254* (2013.01); *A61B 8/445* (2013.01); *A61B 8/461* (2013.01); *A61B 8/486* (2013.01); *A61B 8/488* (2013.01); *A61B 8/5223* (2013.01); *A61B 18/1482* (2013.01); *A61B 8/5215* (2013.01)

(56) References Cited

U.S. PATENT DOCUMENTS

| | | |
|---|---|---|
| 6,006,127 A | 12/1999 | Van Der Brug et al. |
| 6,569,098 B2 | 5/2003 | Kawchuk |
| 6,837,855 B1 | 1/2005 | Puech |
| 6,889,075 B2 | 5/2005 | Marchitto et al. |
| 7,615,015 B2 | 11/2009 | Coleman |
| 7,706,882 B2 | 4/2010 | Francischelli et al. |
| 7,917,312 B2 | 3/2011 | Wang et al. |
| 7,967,742 B2 | 6/2011 | Hoeg et al. |
| 8,183,745 B2 | 5/2012 | Trolier-McKinstry et al. |
| 9,375,196 B2 | 6/2016 | Zheng et al. |
| 2004/0221853 A1 | 11/2004 | Miller |
| 2005/0143662 A1 | 6/2005 | Marchitto et al. |
| 2005/0217381 A1 | 10/2005 | Falk |
| 2006/0036162 A1 | 2/2006 | Shahidi et al. |
| 2006/0184042 A1 | 8/2006 | Wang et al. |
| 2007/0239007 A1 | 10/2007 | Silverman et al. |
| 2009/0088634 A1 | 4/2009 | Zhao et al. |
| 2009/0216129 A1 | 8/2009 | Lasser et al. |
| 2009/0287223 A1 | 11/2009 | Pua et al. |
| 2009/0318756 A1 | 12/2009 | Fisher et al. |
| 2010/0217117 A1 | 8/2010 | Glossop et al. |
| 2011/0106052 A1 | 5/2011 | Chiang et al. |
| 2011/0230710 A1 | 9/2011 | Hoeg et al. |
| 2012/0010506 A1 | 1/2012 | Ullrich |
| 2012/0071757 A1 | 3/2012 | Salcudean et al. |
| 2012/0136242 A1 | 5/2012 | Qi et al. |
| 2013/0218024 A1 | 8/2013 | Boctor et al. |

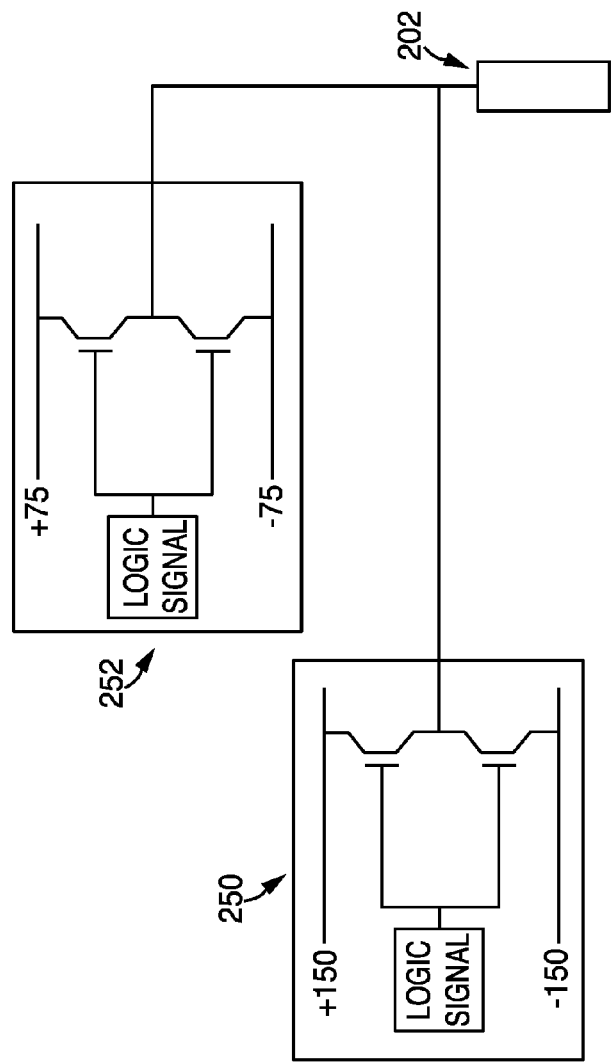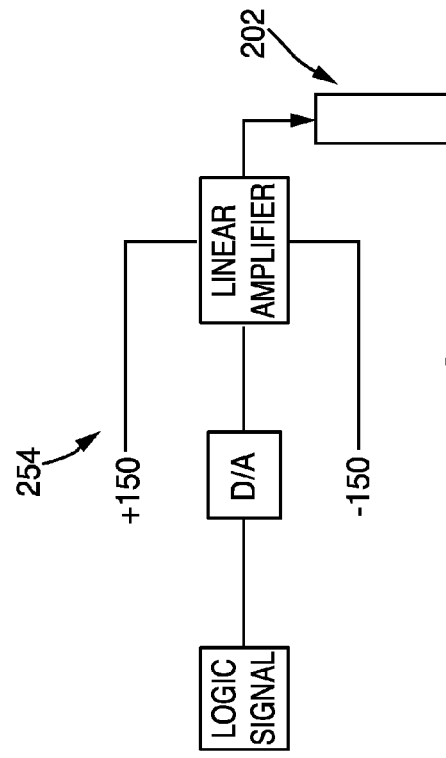
FIG. 11A
FIG. 11B

SYSTEM AND METHOD FOR DETECTING CRITICAL STRUCTURES USING ULTRASOUND

CROSS-REFERENCE TO RELATED APPLICATION

This application is a continuation application of U.S. patent application Ser. No. 13/839,562, filed on Mar. 15, 2013, which claims the benefit of U.S. Provisional Patent Application Ser. No. 61/670,713, filed on Jul. 12, 2012, the entire contents of which are hereby incorporated by reference.

TECHNICAL FIELD

The present disclosure relates to open or endoscopic surgical instruments and methods for treating tissue. More particularly, the present disclosure relates to a system and method for medical imaging and detecting critical structures and their proximity to a surgical device.

BACKGROUND OF RELATED ART

A hemostat or forceps is a simple pliers-like tool that uses mechanical action between its jaws to constrict vessels and is commonly used in open surgical procedures to grasp, dissect and/or clamp tissue. Electrosurgical forceps utilize both mechanical clamping action and electrical energy to affect hemostasis by heating the tissue and blood vessels to coagulate, cauterize and/or seal tissue.

Over the last several decades, more and more surgeons are replacing traditional open methods of gaining access to vital organs and body cavities with endoscopes and endoscopic/laparoscopic techniques and instruments that access organs through small puncture-like incisions. Endoscopic instruments are inserted into the patient through a cannula, or port that has been made with a trocar. Typical sizes for cannulae range from three millimeters to twelve millimeters. Smaller cannulae are usually preferred, which, as can be appreciated, ultimately presents a design challenge to instrument manufacturers who must find ways to make surgical instruments that fit through the cannulae.

By utilizing an electrosurgical instrument, a surgeon can cauterize, coagulate/desiccate and/or simply reduce or slow bleeding, by controlling the intensity, frequency and duration of the electrosurgical energy applied through the jaw members to the tissue. Typically, electrodes, housed in each of the jaw members are charged to a different electric potential such that when the jaw members grasp tissue, electrical energy can be selectively transferred from one electrode to the other and through the tissue.

Bipolar electrosurgical instruments are known in the art. Commonly-owned U.S. Patent Application Publication No. 2007-0062017, discloses an exemplary bipolar electrosurgical instrument. Conventional bipolar electrosurgical instruments may include a cutting blade, fluid applicator, stapling mechanism or other like feature, in various combinations.

During certain procedures, surgeons must identify certain anatomical structures such as large vasculature, bile ducts, or urinary ducts such as the ureter. These structures often need to be avoided or in some instances ligated during a procedure, thus requiring a high degree of confidence when identifying such structures so that they can be properly avoided or ligated as the situation may merit. In surgery (open or laparoscopic), the surgeon is constantly relating the visualized anatomy they are currently operating on or near to known text book anatomy. This task is most difficult when the target anatomy (or that to be avoided) is obscured by overlying soft tissue. As such, the ability to 'see' what lies below the visual tissue surface is desired.

One issue during laparoscopic procedures in particular, is inadvertently injuring nearby critical anatomical structures due to quick or abrupt movement of instruments within the surgical site, poor visibility, lack of tactile response, confusion of the anatomy from patient to patient, or inadequate control of the instrumentation being utilized to perform the procedure. For example, when performing a laparoscopic cholecystectomy to remove the gallbladder, a particular aspect of the procedure is the identification of the common bile duct.

Similarly, when conducting procedures in the lower abdomen such as hernia repair or hysterectomies, great care should be taken to identify the ureter that connects the kidneys to the patient's bladder. Unfortunately, the ureter is at times obscured by connective tissue, and difficult to identify. These issues associated with identifying relatively small lumen (e.g. ureter, blood vessels, gall ducts, etc.) which at times are located proximal other similarly looking lumen are well known and systems have been devised to address them.

For example, there are several systems which employ the use of a stent or catheter to be placed internal to the structure being identified. Some of these systems utilize a light generator which illuminates the lumen. The illumination can be in the visible spectrum for the doctor to easily recognize or in the infrared (IR) spectrum such that it can be detected using an IR camera. The light, in either event, is received by a camera and the doctor is able to visualize the location of the lumen in question.

Another example of known devices employs a long stent placed into the ureter and extending from the bladder to the kidneys. Using a signal generator, the stent is electrified and produces an electrical field. The cutting or grasping surgical instrument used in the underlying surgical procedure includes one or more sensors which can detect the electrical field and signal an alarm if the cutting or grasping device comes too close to the lumen.

These known systems have several significant drawbacks. The first is that they each require a specialized stent or catheter to be placed within and along the length of the lumen being detected. As a result, use of such devices requires a special surgeon to be employed in the mere placement of the stent or catheter. The placement in such delicate structures is quite difficult and time consuming. The use of an additional surgeon, one who likely is not otherwise involved in the underlying procedure being performed, significantly increases the cost of the procedure being performed. Further the placement is time consuming and thus increases the overall operating time for the patient. Again this increases the costs of the procedure, as well as increasing the time the patient must be sedated. With respect specifically to the detection of the ureter, placement of the stent or catheter can be quite problematic.

Other known systems for detecting structures within the body employ the use of fluorescent dyes or other marker materials, such as radioactive fluids which can be used to detect the location of the desired structure within the body. Again there are shortcomings associated with these systems. The dyes employed often are not detectable through tissue, that is they cannot be easily detected from outside the lumen and are better employed in detecting cysts and polyps within a lumen as is common. Radioactive markers are also used to identify structures within a lumen using often x-ray and other visualization techniques. However, these visualization techniques are often not conveniently useable to identify structures while the surgical procedures described above are on-going.

Yet a further known technique is the use of ultrasound imaging to provide clinicians the ability to image sub-surface structures. Ultrasound imaging relies on different acoustic impedances of adjacent tissue structures to provide the contrast required for imaging—usually without the addition of exogenous contrast agents, though these may be employed to identify particular structures. Current techniques include imaging prior to surgery with a trans-cutaneous probe or in the surgical field with a laparoscopic probe. Ultrasound imaging possesses several key advantages over other modes of imaging (e.g., CT, MRI, etc.) which make it very attractive for real-time application in surgery.

The advantages of ultrasound imaging as compared to MRI and CT scans include the necessary hardware being relatively small and inexpensive. Further, the radiation levels imparted on the patient as well as clinicians is considered inherently safe which is not necessarily true for CT. Further, the data is collected instantly and at the point of use as opposed to requiring the patient be positioned in an imaging vessel.

A variety of modes of operation for ultrasound imaging have been developed over the years include A-Mode, B-Mode, M-Mode and Doppler. A-mode (amplitude mode) is the simplest type of ultrasound. A single transducer scans a line through the body with the echoes plotted on screen as a function of depth. In B-mode (brightness mode) ultrasound, a linear array of transducers simultaneously or sequentially scans a plane through the body that can be viewed as a two-dimensional image on screen. In M-mode (motion mode) ultrasound, a single scan line is repeatedly sampled in the same location. The brightness representation of each scan in time is drawn vertically either from left to right on screen or in a fixed location on screen with the older results shifting to the left in a trailing update mode. Over time, this is analogous to recording a video in ultrasound. As the organ boundaries that produce reflections move relative to the probe, this can be used to determine the velocity of specific organ structures. Doppler mode makes use of the Doppler Effect in measuring and visualizing blood flow. In general, whether employing Color Doppler, Power Doppler, or Pulsed Wave Doppler, by calculating the frequency shift of a particular sample volume, for example flow in an artery or a jet of blood flow over a heart valve, the speed of the fluid and its direction can be determined and visualized. In for example, Pulsed Wave Doppler, velocity information is presented as a color coded overlay on top of a B-mode image. Other modes and combinations of modes are also employed in ultrasound imaging, as will be appreciated by those skilled in this art.

There are however, disadvantages to current to ultrasound techniques, particularly the (laparoscopic approaches) which have limited its adoption in minimally invasive surgery. In some of these approaches the image is presented on a separate screen from the laparoscopic image, forcing the surgeon to mentally "shift gears" as they focus on the laparoscope image or the ultrasound image. Current 2-D or even 3-D imaging systems generally seek to provide the highest level of image detail. While this may be useful in the diagnostic phase of care, this is likely more information than is necessary in the real-time treatment venue of an operating room where the questions facing the surgeon are not "What's wrong?" but simply, "Where is it?" Still further in many surgical suites, the required ultrasound cart and probes are simply not available as the need for sub-surface imaging does not exist in every surgical case.

One drawback of current imaging systems is the size and cost of linear imaging arrays comprised of many small piezo electric elements. While they provide detailed images, these probes are costly to manufacture and bulky relative to the size of laparoscopic surgical devices. The present disclosure is directed to addressing these shortcomings of the current systems.

SUMMARY

To address the shortcomings of the current approach to ultrasound imaging, one aspect of the present disclosure is directed to a display with an integrated optical and ultrasound imaging. Further, according to another aspect the information presented to the surgeon is limited to just the most relevant information regarding subsurface structures rather than a full diagnostic image. Still a further aspect of the present disclosure is to integrate the ultrasound imaging transducer into one or more surgical instruments such that the need for a third instrument (and third hand) is eliminated. Additional aspects will also be described herein.

In order to achieve one or more of the advances described above, one of the aspects of the present disclosure is directed to integration of a single ultrasound transducer into an existing laparoscopic device. A single ultrasound transducer can be effectively integrated at low cost, and is useful in paring down the volume of information provided to the surgeon. A single ultrasound transducer provides only a single vector of tissue data at any point in space and time.

One aspect of the present disclosure is directed to a system including a laparoscopic surgical instrument having at least one ultrasound transducer, and a processor adapted to receive acoustic data from the ultrasound transducer and process the acoustic data from the ultrasound transducer to produce a graphical representation of the acoustic data. The graphical representation depicting echoic attributes of tissue substantially axially aligned with a transmission path of the at least one ultrasound transducer, and the distance of at least one tissue type having different echoic attributes from surrounding tissue form a distal tip of the laparoscopic surgical instrument.

According to a further aspect of the present disclosure the graphical representation depicts the location of one or more lumens in axial alignment with the transmission path of the transducer. The graphical representation may depict a lumen with flowing blood or a fluid filled lumen. According to one aspect Doppler ultrasound is employed to identify the direction of flow in the one or more lumens.

The processor may employ A-mode ultrasound, B-mode ultrasound, M-mode ultrasound, Color Doppler ultrasound, or Power Doppler ultrasound to generate the graphical representation.

According to a further aspect of the present disclosure the system includes a tracking element, wherein the tracking element provides data to the processor enabling the processor to determine the location, speed, and direction data of the laparoscopic instrument. The tracking element may be selected from the group consisting of a robotic system, a strobe, a static fiducial element, a trackball affixed to the distal end of the laparoscopic instrument, and an optical motion sensor.

According to a further aspect of the present disclosure, the system may include an optical imaging element outputting an optical image to a display. In certain aspects of the present disclosure the processor incorporates the location, speed and direction data received from the tracking element and outputs to the display a graphical overlay, the graphical overlay registering the movement of the laparoscopic surgical instrument and acoustic data from the ultrasound transducer on the optical image. The portion of the graphical overlay representing movement of the laparoscopic surgical instrument across the optical image may be shown in a first color and the portion of the graphical overlay representing a detected fluid filled lumen may be depicted in a second color.

According to a further aspect of the present disclosure the display further comprises an ultrasound image depicting a cross-sectional view of tissue across which the laparoscopic instrument has been drawn. The ultrasound image may include a graphical overlay depicting one or more lumens. Further the processor may employ Doppler to identify the one or more lumens in the ultrasound image.

A further aspect of the present disclosure is directed to a method including receiving ultrasound data from an ultrasound transducer, processing the ultrasound data to produce a graphical representation depicting echoic attributes of tissue substantially axially aligned with a transmission path of the ultrasound transducer and the distance of at least one tissue type having different echoic attributes from surrounding tissue from a distal tip of a laparoscopic instrument embodying the transducer, and outputting a signal for display of the graphical representation. The graphical representation may depict the location of one or more lumens in axial alignment with the transmission path of the transducer. The graphical representation may depict a lumen with flowing blood and/or a fluid filled lumen. Further, Doppler ultrasound may be employed to identify the direction of flow in the one or more lumens. Still further, the processing may employ A-mode ultrasound, C-mode ultrasound, M-mode ultrasound, Color Doppler ultrasound, or Power Doppler ultrasound.

According to a further aspect of the present disclosure, the method includes tracking the laparoscopic instrument to determine its location, speed and direction. This may also include optically imaging a region of interest and outputting an optical image to a display. The method may further include processing the location, speed and direction of the laparoscopic instrument data and outputting to the display a graphical overlay, the graphical overlay registering the movement of the laparoscopic instrument and acoustic data from the ultrasound transducer on the optical image. The portion of the graphical overlay representing movement of the laparoscopic instrument across the optical image may be shown in a first color and the portion of the graphical display representing a detected fluid filled lumen is depicted in a second color.

According to yet a further aspect of the present disclosure the method includes displaying an ultrasound image depicting a cross-sectional view of tissue across which the laparoscopic surgical instrument has been drawn. The ultrasound image may include a graphical overlay depicting one or more lumens. The method may further employ Doppler processing to identify one or more lumens in the ultrasound image. Still further, the method may include tracking of the laparoscopic surgical instrument to provide data enabling the determination of location, speed and direction data of the laparoscopic instrument. The ultrasound image may be registered with the location, speed, and direction data.

BRIEF DESCRIPTION OF THE DRAWINGS

Various embodiments of the subject system and method are described herein with reference to the drawings wherein:

FIG. 11A is a schematic of a two alternative driver circuit arrangements according to two illustrative embodiments of the present disclosure;

FIG. 11B is a schematic of a further driver circuit arrangement according to one illustrative embodiment of the present disclosure;

DETAILED DESCRIPTION

Figure 1:
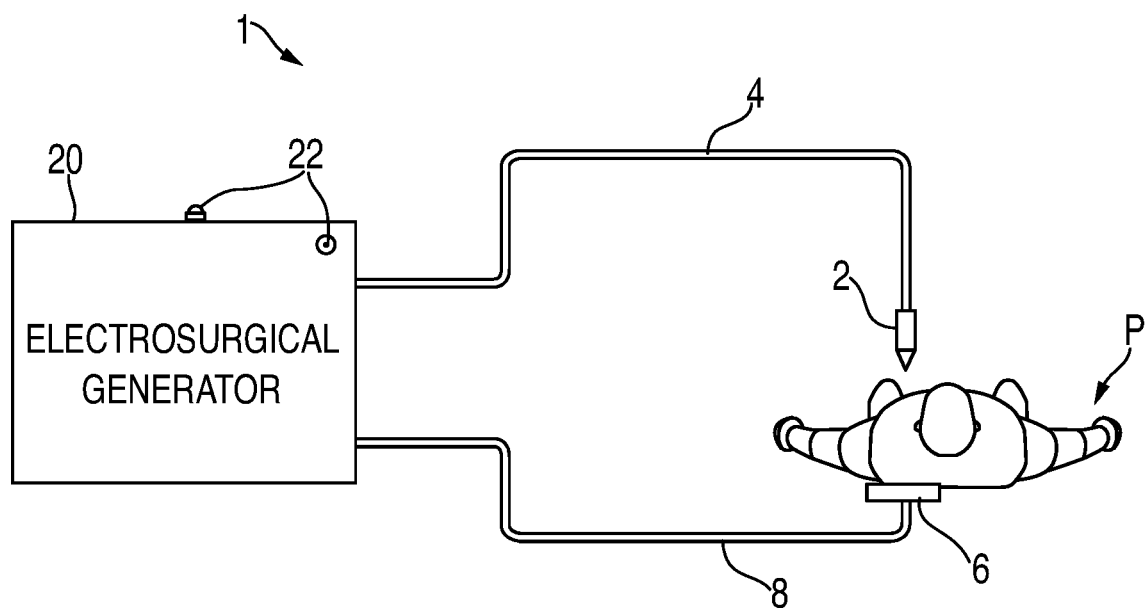
FIG. 1 is a schematic illustration of a monopolar electrosurgical system in accordance with an illustrative embodiment of the present disclosure.

Particular embodiments of the present disclosure are described with reference to the accompanying drawings. In the following description, well-known functions or constructions are not described in detail to avoid obscuring the present disclosure in unnecessary detail. As used herein, the term distal and proximal are with respect to the medical professional utilizing the device or component, with proximal being nearer to the medical professional either when in use or during insertion to the patient. Thus, for example, the distal end of a surgical instrument is that portion nearer the end which will be inserted into a patient and the proximal end is that portion nearer the end which will remain outside the patient, and be available for treatment application by the medical professional.

The present disclosure generally relates to a system for identifying anatomical structures, particularly a lumen such as, for example, a ureter, bile or gall duct, a blood vessel, lymph notes, fluid filed cysts, and the like. In one embodiment the system employs the transmission of an ultrasound signal from one or more transducers, positioned within either a standalone ultrasound wand or a surgical instrument such as a bi-polar forceps. The ultrasound signal is reflected by the boundaries between tissues having different acoustic properties. The reflected signals or echo is received by the transducer and processed. Based on the strength of the returned signal, and the timing of the return, as well as other parameters, anatomical structures can be differentiated from one another and a surgeon can utilize this information to identify structures, and proximity to the structure in question can be gauged. Further, an indication of such proximity can be provided to the surgeon to prevent inadvertent contact with the tissue and to distinguish the tissue to be preserved from tissue that is intended for treatment by the surgeon.

The intraoperative location of critical structures such as blood vessels, lymphatics and ureters is a challenging task confronting the minimally invasive surgeon. In some cases, these structures are the target of the procedure and a faster way to locate them under tissue will save the surgeon time. In other cases where these structures are not the target of the procedure and are at risk of unintentional injury, a means to locate and avoid them will reduce the risk of complications.

According to one embodiment described herein, a simplified version of ultrasonic imaging with a single-element transducer deployed at the distal end of a laparoscopic device. The single-element is very small and inexpensive compared with linear imaging array transducers. The small size allows the placement of this transducer in the operative end of, for example, 5 mm laparoscopic devices. The size and the simplicity of fabrication of the single-element ultrasound transducer allow it to be implemented in a single-use surgical device.

A single ultrasound element having a very narrow beam profile allows the user to interrogate tissue along a vector into the tissue volume. A short electrical pulse is applied to this transducer which converts the electrical signal to mechanical displacement via the piezoelectric effect. The mechanical displacement propagates as a focused wave packet (or beam) through the tissue to be interrogated. As this beam encounters tissue structures with varying acoustic impedance, some of the energy is reflected back to the transducer as echoes. This echo response is digitized with respect to time. Referenced to the time when the pulse is generated, the time of arrival of each successive echo indicates, in a very predictable fashion, the depth of the structure which created the echo. This data can be converted to human readable format and presented to the user on a visual display to show the underlying structure.

Location of blood vessels may be accomplished via sensing a Doppler shift of those reflected echoes which were generated from moving structures such as red blood cells moving in blood vessels. Using, for example, Pulsed Wave Doppler processing, the depth and diameter of a blood vessel encountered by the single beam can be determined and this location can be shown in pseudo color on the display. Regions with blood flow are typically colored red (flow toward the transducer) and blue (flow away from the transducer).

Thus according to one embodiment of the present disclosure, locating ureters or lymphatics is accomplished by recognizing these structures as anechoic regions in the interrogated tissue column. The ureter specifically is a tubular structure with an inside diameter from approx. 1 mm to 4 mm containing urine. The intra-luminal urine has no structure and as such reflects no energy back to the transducer. The echo signature from this region appears black when converted to brightness as in typical ultrasound (B-mode) imagers. Below a threshold, the user display can be pseudo-colored to facilitate location of this structure. Contrasted against vessel detection methods relying on the strong wall echoes, this approach is very robust to the angle of the transducer incident upon the vessel. This data in combination with the surgeon's awareness of the anatomy and other landmarks in the surgical field provide a very valuable aid to the surgeon. These and other embodiments of the present disclosure are described in greater detail herein.

An electrosurgical generator according to the present disclosure can perform monopolar and bipolar electrosurgical procedures, including anatomical tissue ligation procedures. The generator may include a plurality of outputs for interfacing with various bipolar and monopolar electrosurgical instruments (e.g., laparoscopic electrodes, return electrodes, electrosurgical forceps, footswitches, etc.). Further, the generator includes electronic circuitry configured to generate electrosurgical energy (e.g., RF, microwave, etc.) specifically suited for various electrosurgical modes (e.g., cut, coagulate (fulgurate), desiccate, etc.) and procedures (e.g., ablation, vessel sealing, etc.). Examples of such generators are described hereinabove.

FIG. 1 is a schematic illustration of a monopolar electrosurgical system 1. The system 1 includes an electrosurgical instrument 2 having one or more electrodes for treating tissue of a patient P. The instrument 2 may be, as shown in FIG. 1 a monopolar type instrument (e.g., electrosurgical cutting probe, ablation electrode(s), etc.) including one or more active electrodes. Electrosurgical energy is supplied to the instrument 2 by a generator 20 via a supply line 4 of the generator 20, allowing the instrument 2 to coagulate, seal, cut, ablate, and/or otherwise treat tissue. The electrosurgical energy is returned to the generator 20 through a return electrode 6 via a return line 8.

Figure 2:
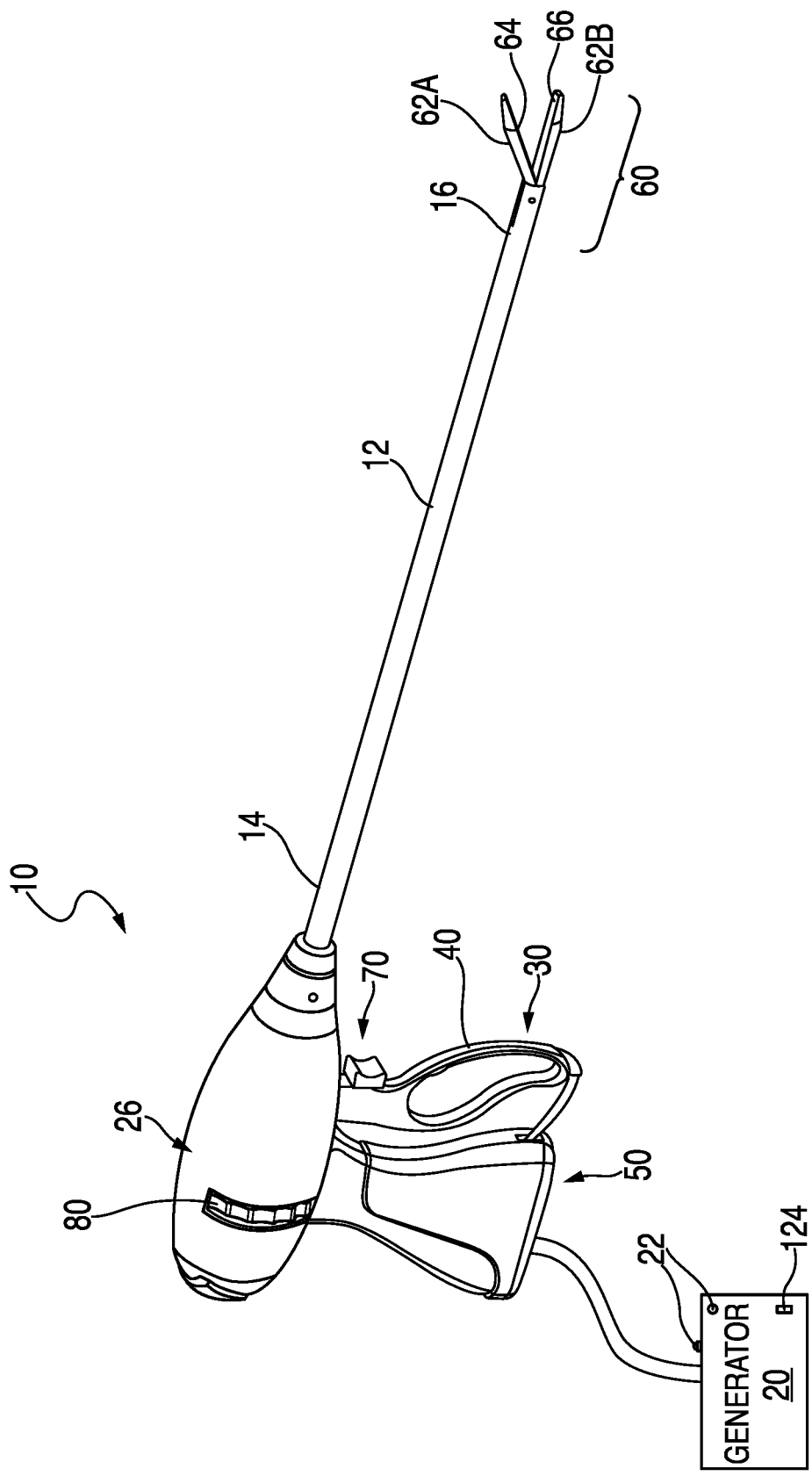
FIG. 2 Fig. is a perspective view of a bipolar electrosurgical system in accordance with an illustrative embodiment of the present disclosure.

FIG. 2 depicts a bipolar forceps 10 which may be used for a variety of coagulation and vessel sealing applications. The bipolar forceps 10 includes a housing 26, a handle assembly 30, a rotating assembly 80, a trigger assembly 70, and an end effector assembly 60 that mutually cooperate to grasp, seal, and divide tissue such as tubular vessels and vascular tissues. Forceps 10 includes a shaft 12 that has a distal end 16 dimensioned to mechanically engage the end effector assembly 60 and a proximal end 14 that mechanically engages the housing 20. The end effector assembly 60 includes opposing jaw members 62a, 62b that cooperate to effectively grasp tissue for sealing purposes. With this purpose in mind, jaw members 62a, 62b include at least one active electrode 64 and at least one return electrode 66 disposed thereon in a bipolar configuration. Active electrode 64, and return electrode 66 are operably coupled to generator 20 and are configured to selectively apply electrosurgical energy supplied from the generator 20 to tissue grasped between the jaw members 62a, 62b. The end effector assembly 60 may be designed as a unilateral assembly, e.g., jaw member 62b is fixed relative to the shaft 12 and jaw member 62a pivots relative to jaw member 62b to grasp tissue, or as a bilateral assembly, e.g., jaw members 62a and 62b pivot relative to each other to grasp tissue.

Examples of forceps are shown and described in commonly-owned U.S. application Ser. No. 10/369,894 entitled "VESSEL SEALER AND DIVIDER AND METHOD MANUFACTURING SAME" and commonly-owned U.S. application Ser. No. 10/460,926 (now U.S. Pat. No. 7,156, 846) entitled "VESSEL SEALER AND DIVIDER FOR USE WITH SMALL TROCARS AND CANNULAS".

Although the following disclosure focuses predominately on discussion of electrosurgical instruments for use in connection with endoscopic surgical procedures, open type instruments are also contemplated for use in connection with traditional open surgical procedures. Thus, and as described in greater detail below, the aspects of the present disclosure may be incorporated into any suitable electrosurgical instrument (e.g., instrument 2, forceps 10) or suitable non-electrosurgical instrument (e.g., probes, graspers, prods, clamps, grips, forceps, pliers, cutters, devices, etc.).

Figure 3:
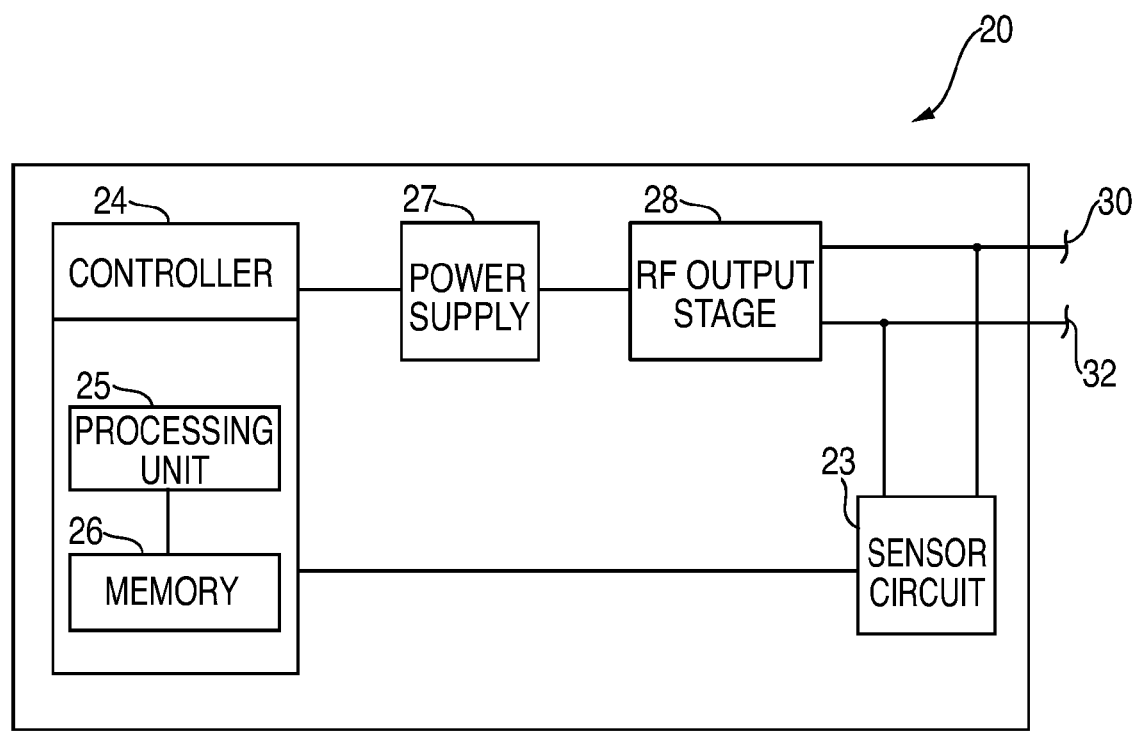
FIG. 3 is a schematic block diagram of a generator in accordance with an illustrative embodiment of the present disclosure.

FIG. 3 shows a schematic block diagram of the generator 20 having a controller 24, a high voltage DC power supply 27 ("HVPS"), a sensor module 23, and an energy output stage 28 (e.g., an RF output stage) configured to output electrosurgical energy (e.g., microwave, RF, etc.) from generator 20. Examples of such a generator are described in detail in commonly assigned U.S. Pat. No. 7,972,328 entitled "System and Method for Tissue Sealing." The HVPS 27 is connected to a conventional AC source (e.g., electrical wall outlet) and provides high voltage DC power to the energy output stage 28, which then converts high voltage DC power into electrosurgical energy for delivery to the active electrode(s) of an electrosurgical instrument (e.g., instrument 2, forceps 10, etc.) via the active terminal 30. In certain embodiments, the electrosurgical energy is returned to the generator 20 via the return terminal 32.

The generator 20 may include a plurality of connectors to accommodate various types of electrosurgical instruments (e.g., instrument 2, electrosurgical forceps 10, etc.). Further, the generator 20 may operate in monopolar or bipolar modes by including a switching mechanism (e.g., relays) to switch the supply of electrosurgical energy between the connectors, such that, for instance, when the monopolar type instrument 2 is connected to the generator 20, only the monopolar plug receives electrosurgical energy.

The controller 24 includes a processing unit 25 operably connected to a memory 26, which may be volatile type memory (e.g., RAM) and/or non-volatile type memory (e.g., flash media, disk media, etc.). The processing unit 25 may be any logic processor or analog circuitry (e.g., microprocessor, control circuit, ASIC, FPGA, etc.) adapted to perform the calculations discussed in the present disclosure. The processing unit 25 includes an output port that is operably connected to the HVPS 27 and/or the energy output stage 28 allowing the processing unit 25 to control the output of the generator 20 according to either open and/or closed control loop schemes.

A closed loop control scheme generally includes a feedback control loop wherein the sensor module 23 provides feedback to the controller 24 (e.g., information obtained from one or more sensing mechanisms that sense various tissue parameters such as tissue impedance, tissue temperature, tissue conductivity, tissue permittivity, output current and/or voltage, etc.). The controller 24 then signals the power supply 27, which then adjusts the DC power supplied to the RF output stage 28, accordingly. The controller 24 also receives input signals from the input controls of the generator 20 and/or instrument 2 or forceps 10. The controller 24 utilizes the input signals to adjust the power output of the generator 20 and/or instructs the generator 20 to perform other control functions. In some embodiments, the generator 20 may utilize audio-based and/or a video-based display to inform the user of the sensed tissue parameters in the field of view of the one or more sensing mechanisms.

The processing unit 25 is capable of executing software instructions for processing data received by the sensor module 23, and for outputting control signals to the generator 20 or other suitable operating room devices (e.g., camera monitor, video display, audio output, etc.), accordingly. The software instructions, which are executable by the controller 24, are stored in the memory 26 of the controller 24. The controller 24 may include analog and/or digital logic circuitry for processing the sensed values and determining the control signals generated by the controller 24 and sent to the power supply 27 or RF output stage 28.

In some embodiments, generator 20 and processing unit 25 may be separate stand-alone units operably connected to each other (not shown) or processing unit 25 may be incorporated within generator 20, as shown in FIG. 2. In some embodiments, generator 20 (including processing unit 25) may be incorporated within the surgical device being used during a procedure (i.e., instrument 2 or forceps 10 may be battery powered and include an on-board generator). In this scenario, the signal-to-noise ratio of signals transmitted to and from processing unit 25 may be improved since the signals may experience a decrease in losses caused by travel through relatively long lengths of cable. For ease of disclosure, generator 20 is described as incorporating processing unit 25 as depicted in FIGS. 1-3.

Figure 4A:
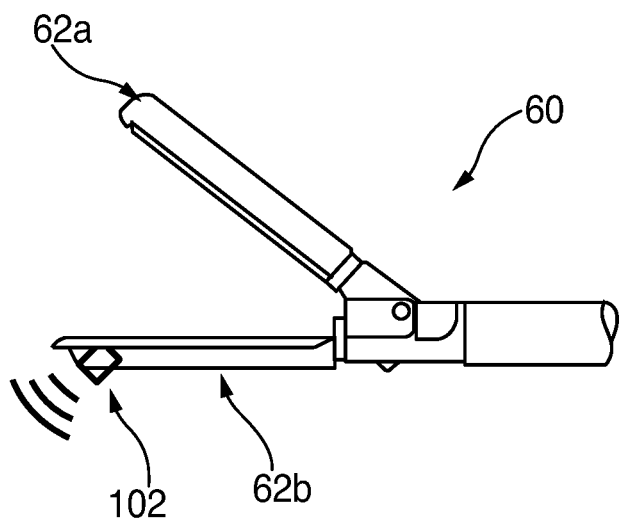
FIG. 4A is a partial profile view of distal portions of an end effector of a surgical instrument according to an illustrative embodiment of the present disclosure.
Figure 4B:
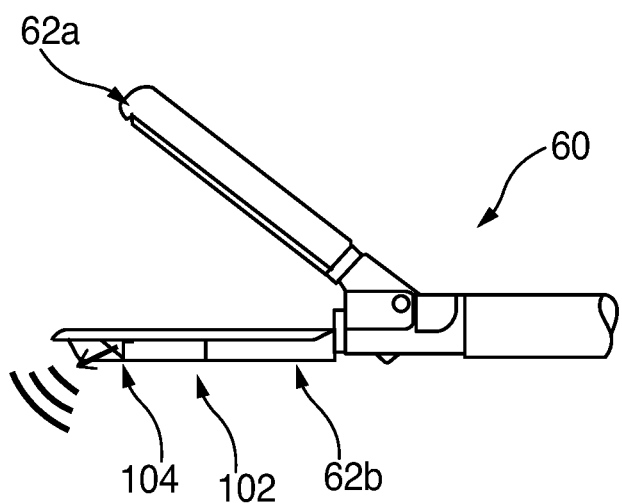
FIG. 4B is a partial profile view of distal portions of an end effector of a surgical instrument according to an illustrative embodiment of the present disclosure.

FIGS. 4A-4D depict three variations of a single ultrasound transducer 102 implemented within the end effector 60 of a laparoscopic surgical instrument. In FIGS. 4A-4D the ultrasound transducer 102 is housed within the fixed jaw member 62b. As will be appreciated, the ultrasound transducer 102 could alternatively be in the movable jaw member 62a. Placement in the moveable jaw provides the benefit of articulation of the transducer axis relative to the device shaft allowing the user to approach a wider range of tissue surfaces given the constraint of the port placement. In FIG. 4A, the ultrasound transducer 102 is configured as a direct fire device oriented at an angle to the longitudinal axis of the lower jaw member 62b. This angle allows for the transducer 102 to focus energy on the tissue that is directly in front of a slightly below the fixed jaw member 62b. As a result, the imaging produced is of the tissue which is in the line of travel of the laparoscopic instrument when travelling in the distal (away from the surgeon) direction, further this angle helps ensure that the energy from the transducer 102 to be applied nearly perpendicularly to the structure of interest, despite the laparoscopic instrument being constrained by a trocar. The ultrasound transducer 102 in FIG. 4B accomplishes the same imaging as that shown in FIG. 4A. However the ultrasound transducer in FIG. 4B is in line with the longitudinal axis of the fixed jaw 62b. Rather than angling the ultrasound transducer 102, an acoustic waveguide 104 is employed which angles the energy emitted from the ultrasound transducer 102 so that it functions similarly to the angle ultrasound transducer 102 of FIG. 4A. This allows integration into the jaw member of a transducer with a physically longer structure without impacting the shape and primary function of the jaw.

Figure 4C:
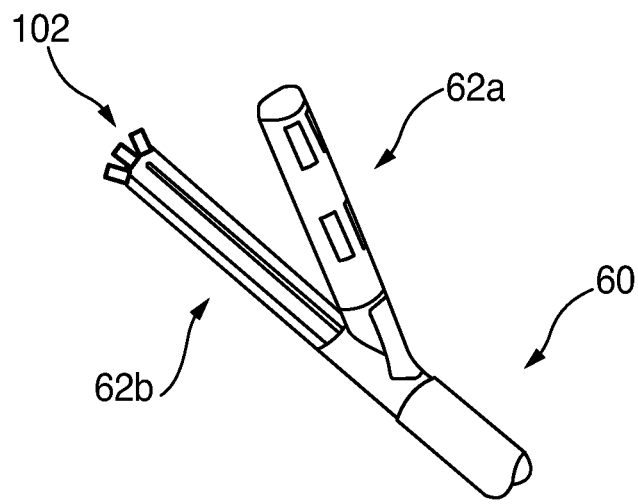
FIG. 4C is a perspective view of a distal portion of an end effector of a surgical instrument according to an illustrative embodiment of the present disclosure.
Figure 4D:
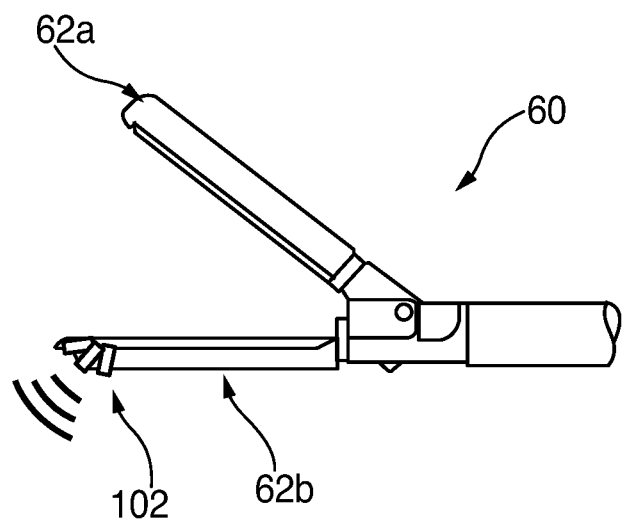
FIG. 4D are a profile view of an end effector of a surgical instrument according to an illustrative embodiment of the present disclosure.

FIGS. 4C and 4D depict an ultrasound arrangement including multiple transducers 102 configured as a phased array. FIG. 4C shows a phased array oriented to scan a sector within the plane parallel to the fixed jaw face. FIG. 4D shows a phased array oriented to scan a sector within the plane perpendicular to the fixed jaw face and including the device shaft. Multiple transducers can be beneficial in expanding the area being scanned by the ultrasound energy as compared to the area scanned by a single transducer. Further, the use of multiple transducers allows for more complicated processing to be undertaken where the returned signals gathered by each transducer are both combined to provide a wider area of scan, and compared to resolve images with greater resolution. These aspects of the present disclosure are described in greater detail below.

Figure 5:
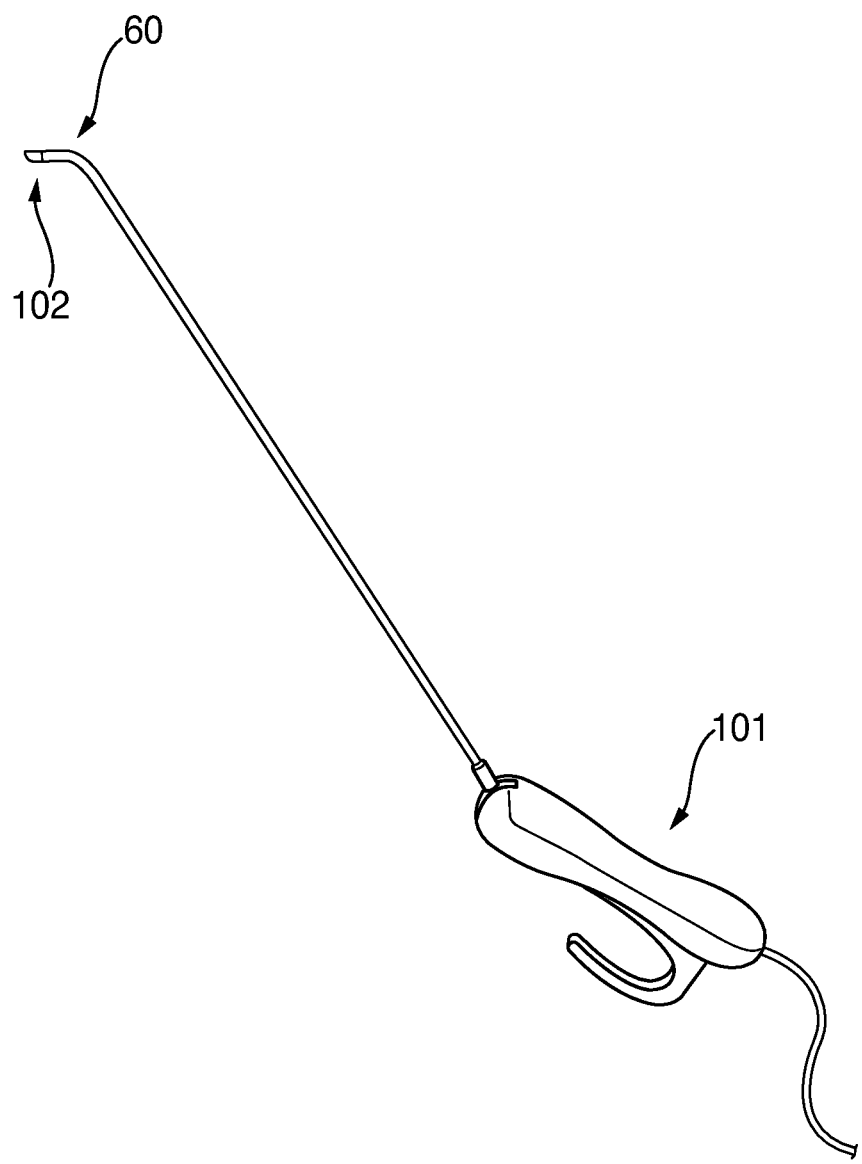
FIG. 5 is a perspective view of an ultrasound probe according to a further illustrative embodiment of the present disclosure.

FIG. 5 shows an alternative embodiment of the present disclosure where the ultrasound transducer 102 is embodied in an articulating end effector 60 at the end of a dedicated ultrasound probe 101. The articulation assists the surgeon in orienting the ultrasound transducer 102 normal to the tissue surface. The dedicated ultrasound probe 101 may be powered by a generator 20, as shown in FIG. 2, or may be battery powered. As shown in FIG. 5, the end effector 60 is articulated such that it can be moved in a various directions to interrogate tissue in the direction that the transducer 102 is pointing. The sole function of the probe 101 is to position and manipulate the tissue surface within the laparoscopic surgical environment. This probe 101 is typically inserted into a patient through a trocar (not shown). The articulation is optional, and it will be understood by those of skill in the art that an unarticulated probe 101 could also be employed.

Figure 6:
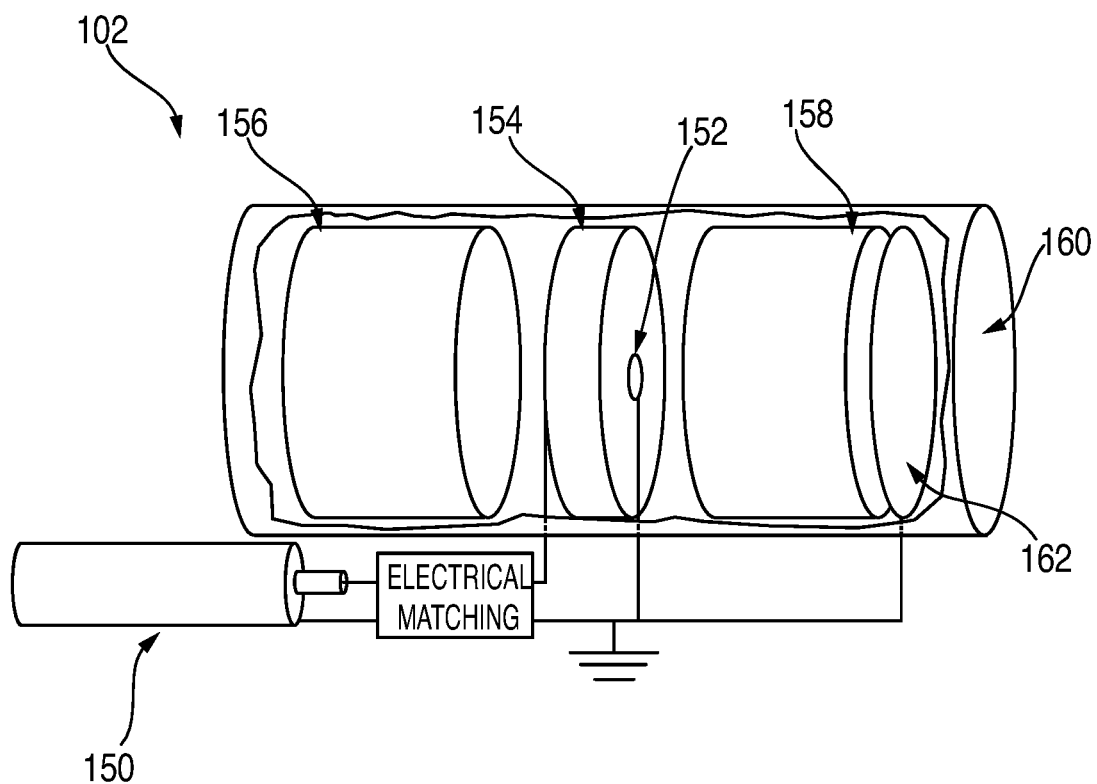
FIG. 6 is an exploded view of an ultrasound transducer according to one illustrative embodiment of the present disclosure.
Figure 7A:
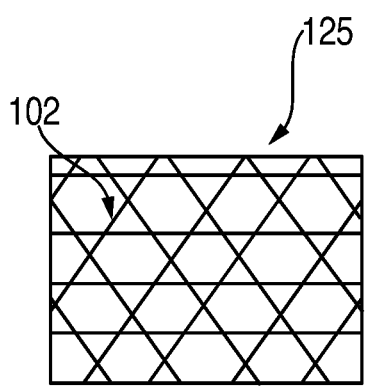
FIG. 7A depicts an ultrasound material and method of forming hexagonal transducer according to an illustrative embodiments of the present disclosure.
Figure 7B:
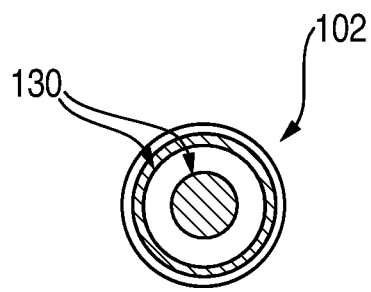
FIG. 7B depicts an alternative ultrasound transducer arrangements according to an illustrative embodiments of the present disclosure.

FIG. 6 depicts an ultrasound transducer 102 according to one embodiment of the present disclosure. In FIG. 6, the single ultrasound transducer 102 is depicted as a "cylindrical" or "piston-type" transducer. However, other types of ultrasound transducers and known and within the scope of the present disclosure. For example, as shown in FIGS. 4A and 4B the ultrasound transducer 102 may be rectangular or square, which is an inexpensive method of manufacturing them as it requires just linear dicing of a raw material sheet of transducer material. Further, a balance between the beam performance achieved with a cylindrical transducer and the cost-effective nature of a square or rectangular transducer can be found in a hexagonal shaped transducer as shown in FIG. 7A. The hexagonal shape is "almost round" thus has better beam performance than square, but can be manufactured by a three pass linear cutting process as shown in FIG. 7A. Yet a further arrangement can be an annular array as shown in FIG. 7B wherein multiple concentric high voltage electrodes 130 are patterned on the back of the transducer 102 (same crystal). Such an arrangement allows for time delayed excitation of the electrodes which assists in the shaping of the beam profile.

Returning to the cylindrical arrangement of FIG. 6, the ultrasound transducer 102 includes a source of RF energy 150, depicted as a coaxial cable. An alternating electric signal is applied to electrodes 152, which are formed on opposing faces of the transducer crystal 154. A backing material 156 provides a highly-damped face on the back of the transducer crystal 154 to ensure efficient coupling of the mechanical energy in to the tissue which in operation would be to the right of the transducer 102 as shown in FIG. 6. A matching layer 158 having acoustic impedance in between that of the transducer crystal 154 and that of the tissue (not shown) is employed to ensure efficient coupling of the mechanical energy into the tissue. In some cases, two matching layers 158 employed in layers to increase the bandwidth of the ultrasound transducer 102. A fully enclosed conductive noise shield 160 is employed to limit the coupling of stray electrical interference into the coaxial cable which will ultimately enter a very sensitive (high gain) receiver. Such a noise shield 160 can be very importation where robust detection of anechoic regions relies on a low system electrical noise floor. The noise shield 160 may be, for example, a sputter-coated gold coating or another conductive metal (i.e. copper or stainless steel) structure and can also server as a mechanical attachment point of the ultrasound transducer 102 to an electrosurgical device 10 or probe 101. In certain embodiments an additional noise shield 162 may be employed. Further, a Parylene or other insulating layer may be applied over the RF hot contact of the transducer crystal 154 to allow the assembly to pass high potential testing which may be necessary for safety reasons.

The transducer crystal 154 may be formed of a variety of different materials. For example, the transducer crystal 154 may be made of Lead Zirconate Titanate (PZT). PZT is the least expensive option based on the current cost of raw materials. However, PZT is also the material with the lowest level of performance. Specifically, the sensitivity and bandwidth are lower than composite materials. A composite material involves starting with raw PZT and dicing very fine lines across its surface and then filling these lines with an epoxy material. The result of this processing is higher sensitivity and increased bandwidth; however, it also comes at a higher cost in view of the extra processing steps. Finally CMUT (capacitive micro-machined ultrasonic transducers) can also be employed. CMUT's can achieve performance (sensitivity and bandwidth) as high as or higher than standard PZT. This technology is based on semiconductor manufacturing techniques and has a very high initial cost to develop the design and tooling but can achieve very low per-piece cost. Additionally, however, the use of CMUT's requires different and more complicated driving electronics.

One of the goals of the system and devices according to the present disclosure is the ability to resolve small (1 mm) anechoic regions without coupling substantial energy on either side of the vessel as the return of such a substantial energy signal would appear as signal above desired thresholds. The ideal beam for such an application would be infinitely narrow along the axis into tissue. As such an ideal beam is not possible with existing ultrasound technology, tradeoffs and strategies to optimize the performance must be considered.

Imaging depth is one consideration. According to at least one embodiment of the present disclosure, imaging performance of a few centimeters into the underlying tissue is sufficient. Tissue strongly attenuates the ultrasound energy and eventually the amplitude of the returning echoes from depth falls below the noise floor of the electronics and a signal can no longer be extracted. As a result, there are a variety of strategies to increase imaging depth. First a lower transmission center frequency can be employed. However, this technique comes at the expense of axial resolution. Another approach is to include more pulses in the transmit sequence. This technique too comes at the expense of axial resolution. Alternatively, a higher transmission amplitude (up to the FDA mandated maximum) can be used. Yet a further variation employs coded excitation. In coded excitation, the pulse envelope is modulated in a way the receiver can mask to discriminate signal from noise without loss of axial resolution. Still further, a larger diameter transducer crystal can be used, but such an implementation comes at the expense of lateral resolution in the near field, as well as concerns with respect to mounting the transducer with in the probe 101 or electrosurgical device 10.

As noted above, axial resolution is another of the considerations. Axial resolution refers to the ability to discern small structural differences along the ultrasound beam. The system and devices according to the present disclosure must resolve structure as small as 1 mm. This requires an axial resolution several times smaller than 1 mm (e.g., approx. 200 μm). A variety of strategies to improve axial resolution are contemplated. In a first strategy a higher transmission center frequency can be employed. However, this higher transmission center frequency comes at the expense of imaging depth. Alternatively, the pulse shape can be using for example a multi-level or linear transmitter as will be discussed in greater detail below. The linear transmitter in particular may employ a Gaussian envelope to match transducer impulse response, by creating a nearly sinusoidal RF signal that is applied to the transducer. Yet a further method employs coded excitation. In coded excitation, the pulse envelope is modulated in a way the receiver can mask to discriminate signal from noise without loss of axial resolution.

Lateral resolution is yet a further of the considerations. As noted above, the ideal beam is infinitely narrow along its axis. Real ultrasound beams begin at roughly the diameter of the transducer face. The beam then narrows to a natural focus after which it tends to diverge indefinitely as the beam reaches depth in tissue. According to the system and devices of the present disclosure, it is preferable that at least a minimum cystic resolution is achieved As above, trade-offs affect the near field and far field regions of the beam differently. According to one embodiment the system of the present disclosure achieves a cystic resolution of less than five mm, preferably less than 3 mm and more preferably about 1 mm. A 1 mm cystic resolution is one that can resolve a 1 mm anechoic area (e.g., fluid filled vessel of about 1 mm diameter or fluid filled cyst of about 1 mm diameter) in a generally scattering background, such as tissues commonly found in the bodies of mammals. 1 mm is approximately the intraluminal diameter of the ureter and other ducts in adult humans. One of skill in the art will recognize that greater resolution i.e., identification of a smaller diameter anechoic area could also be achieved without departing from the scope of the instant disclosure.

With respect to near field beam width, one method of improving the energy retained within the beam width is to use a smaller transducer diameter. However, the use of a small diameter transducer has a negative effect on the imaging depth achievable. Alternatively, a lower frequency transmission can be employed. The lower frequency shortens the near field/far field crossover distance (focal point) from the face of the transducer, but use of lower frequency comes at the expense of axial resolution. Further, transmit apodization has been contemplated. Apodization can be accomplished in a single transducer crystal where the high voltage electrode is patterned with a shape which concentrates the electric field in the crystal in the center as opposed to uniformly across the diameter. Apodization can reduce the appearance of a 'double peak' in the near field. Yet a further approach to managing the beam width can be seen with respect to FIG. 7B, where an annular array of two distinct electrodes is employed. By delaying the signal applied to each electrode, the focus of an ultrasound beam generated by the annular transducers can be varied (i.e. focused).

With respect to far field beam width, strategies to improve (narrow) the beam width include using a larger diameter transducer. However a larger transducer comes at the expense of near field beam width, as well as issues with respect to integration into a probe 101 or electrosurgical device 10. Also, a higher frequency can be employed to maintain a narrow beam over a longer distance, however, this comes at the expense of overall imaging depth. In view of these conflicting considerations, one of skill in the art would be able to design an optimal transducer of the appropriate size, being driven at an optimal frequency and amplitude to identify the tissue of concern, for example the ureter, lymphatic's, or other lumen occurring within the body.

Figure 8:
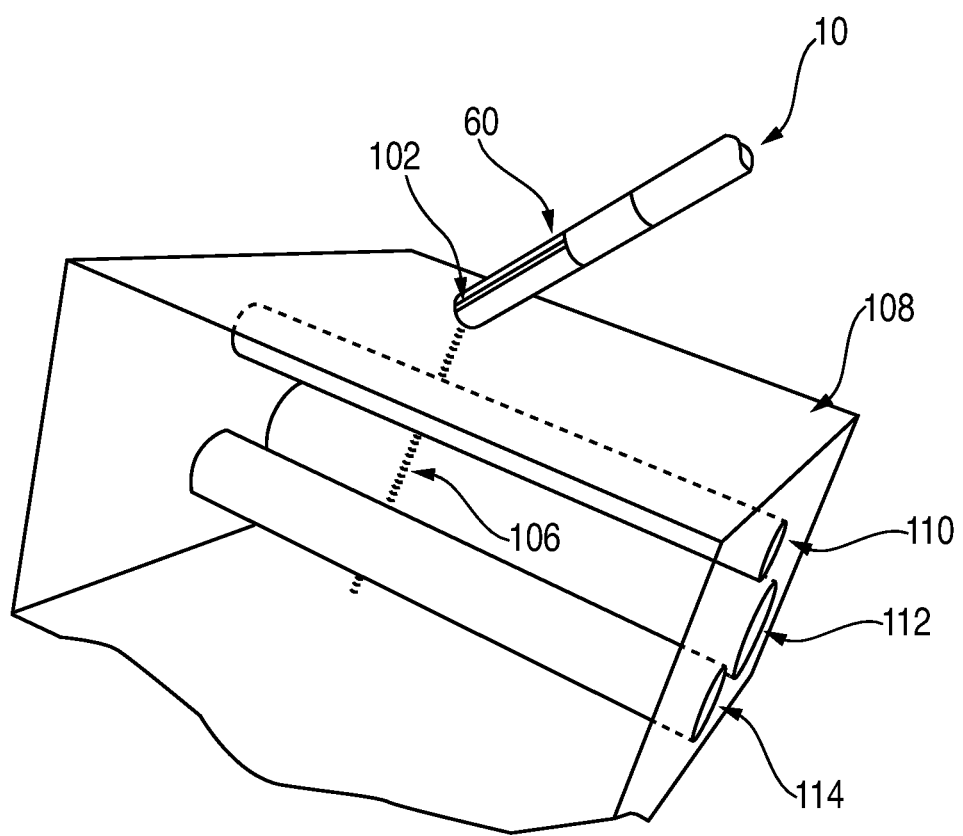
FIG. 8 is a perspective view of an electrosurgical instrument interrogating tissue according to one illustrative embodiment of the present disclosure.

FIG. 8 depicts the operation of one embodiment of the present disclosure. As shown in FIG. 8, an electrosurgical device 10, with an end effector 60 including an ultrasonic transducer 102. The ultrasonic transducer 102 generates an ultrasonic (acoustic) pulse or beam depicted generally as line 106. The ultrasound transducer 102 should generally contact the tissue 108, or be connected through a fluid such as saline, as an air gap between the ultrasound transducer 102 and the tissue 108 interferes with the operation of the ultrasound capabilities. As shown in FIG. 8, the beam 106 only traverses the ureter 110 and the blood vessel 114, thus while the blood vessel 112 is in proximity of the other two lumen, because of the narrowness of the beam 106 generated by the ultrasound transducer 102, its presence may not be detected as it is not in-line with the generated ultrasound beam 106.

Figure 9:
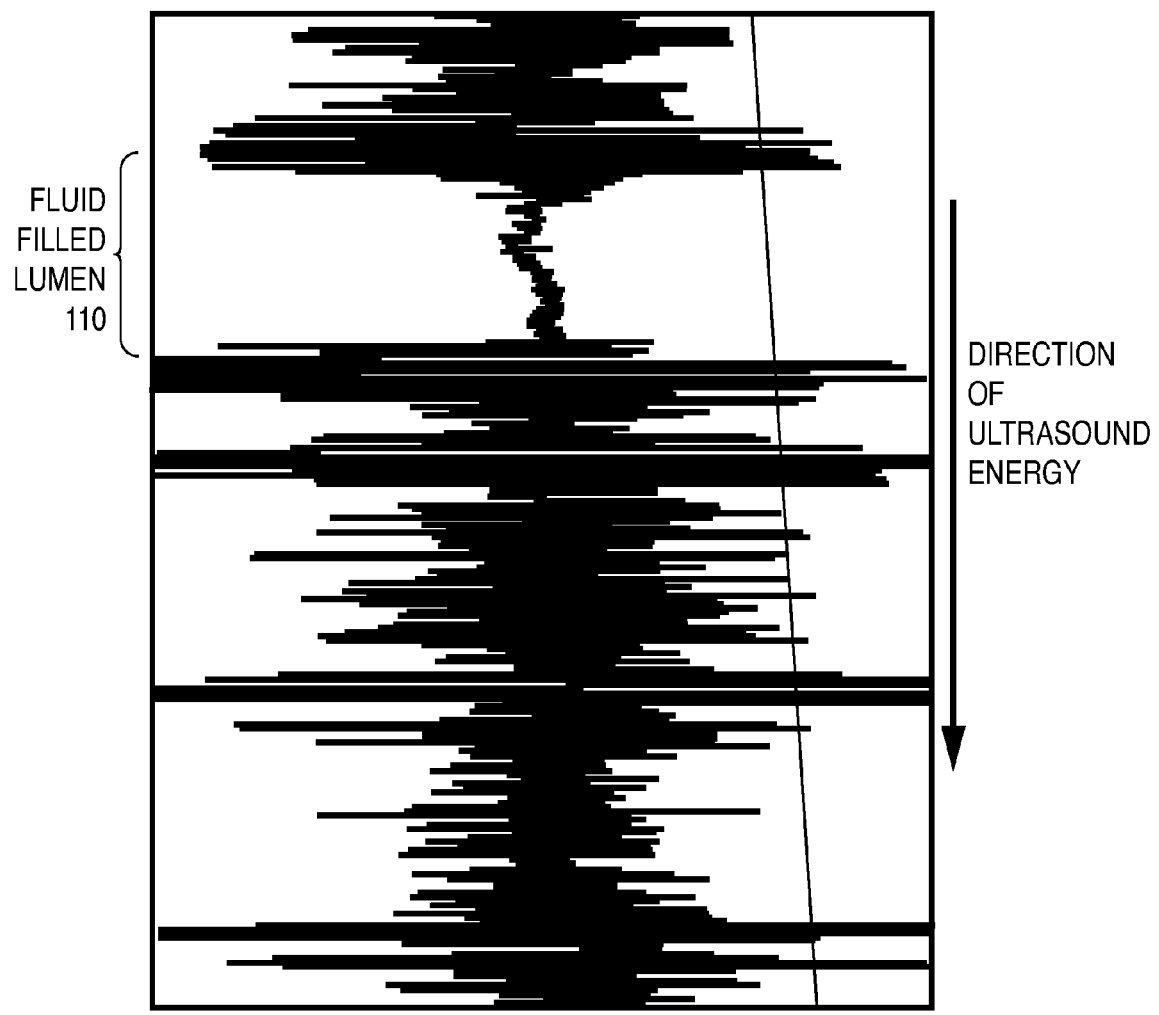
FIG. 9 is an image of an echo response from an ultrasound interrogation signal.

FIG. 9 depicts the presence of a fluid filled lumen in an A-mode scan using a single ultrasound transducer 102, such as that shown in FIG. 6. Fluid within the body is generally less echoic than other materials in the body such as bone, cartilage, and muscle. Thus a fluid filled lumen 110 can often be detected as a location of low backscatter (i.e., a hole in the return data). Particular fluids, such as urine are nearly non-echoic thus a lumen filled with urine such a ureter can be reliably detected as locations of low backscatter as shown in FIG. 9.

Figure 10:
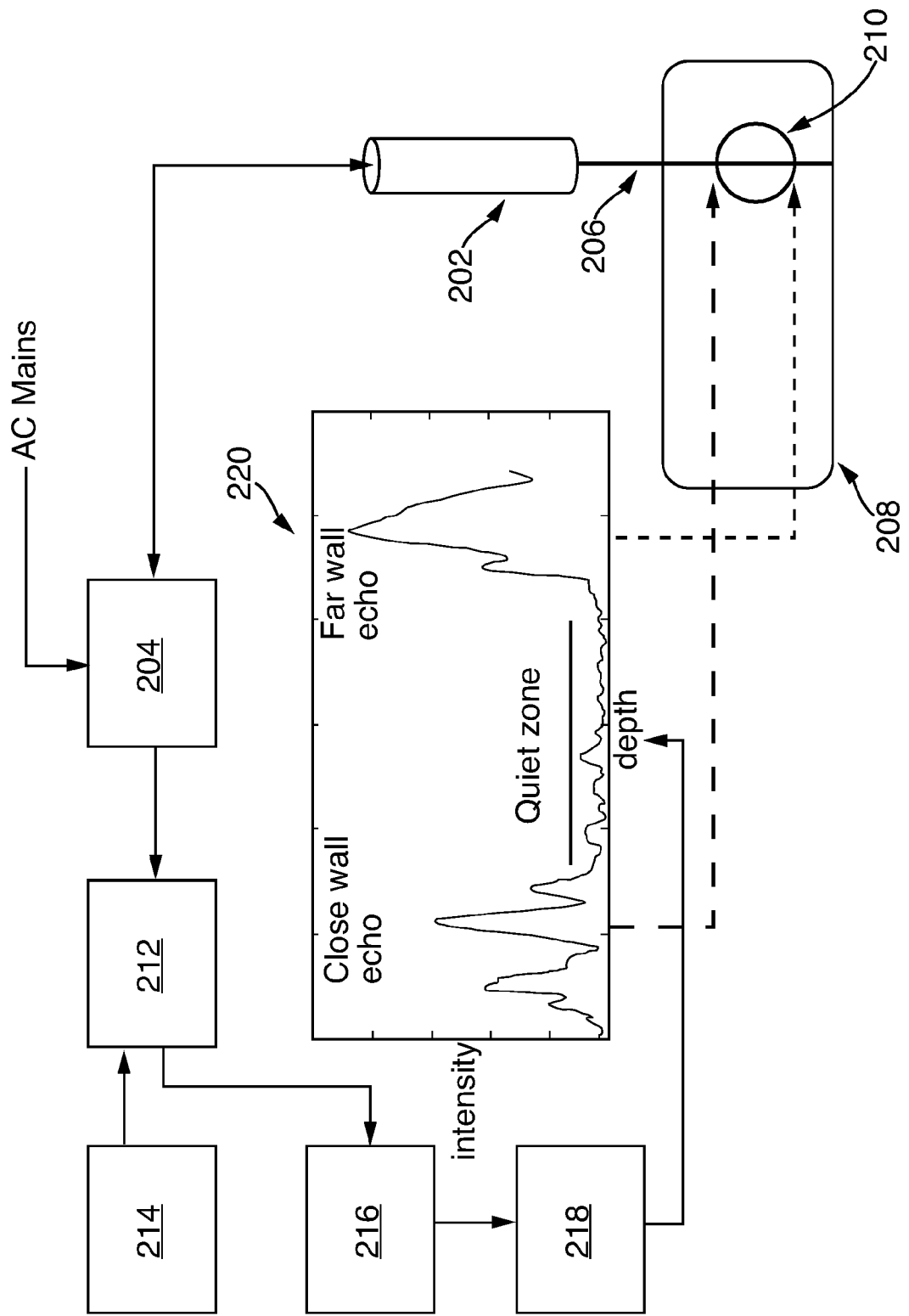
FIG. 10 is a schematic block diagram of an ultrasound system according to one illustrative embodiment of the present disclosure.

FIG. 10 provides a simplified schematic of an ultrasound imaging system as employed according to certain embodiments of the present disclosure. The components depicted in FIG. 10 may reside in, for example the generator 20 shown in FIG. 2, with the exception of the transducer 202, which may reside at the distal end of a probe 101 or electrosurgical instrument 10. As shown in FIG. 10, the AC mains supply AC power to a Pulser/Receiver 204. The Pulser/Receiver 204 can include a power supply (not shown) comprised of a rectifier to convert the AC Mains voltage to DC. In one embodiment the power supply also includes a transformer (either step-up or step-down, depending on AC Mains voltage) is used to achieve a 150V signal. The 150 V signal is then rectified to produce a DC voltage power supply output of +150V and −150V. The power supply may also include an adjustable set-point to reduce the output amplitude for some imaging modes. Dual supply rails may also be employed for the Pulsed Wave Doppler function (discussed in greater detail below) to aid in meeting the maximum acoustic power output limitations imposed by certain regulatory bodies. For example a higher voltage rail may be used to excite the transducer for imaging pulses which last only 1 to a few cycles. A lower voltage rail may be used to excite the transducer for Doppler pulses which may last from about 8 to about 32 or more cycles in order to increase the signal to noise ratio (SNR). In this way the total energy in the pulse sequence can be limited by the rail voltage.

The Pulser/Receiver also includes a transmitter as shown in FIG. 12A or 12B. FIG. 11A actually depicts two different arrangements. The first is a square wave transmitter 250 which is comprised of the +/−150V rails, and two MOSFETs which are driven by a logic signal. As a shown square wave transmitter 250 has one terminal of the transducer 202 connected to the mid-point of the two MOSFETs. The logic signal alternately opens and closes the two MOSFETs so that a 150V square wave is produced. This voltage is then applied to the transducer 202 to cause it to oscillate. As can be appreciated, a square wave is not the ideal energy form to be applied to the ultrasonic transducer 202. Thus a second transmitter 252 may be employed on a second set of power supply rails having, for example, a voltage of +/−75V. The transducer 202 is also connected to the mid-point of the second setoff MOSFETs found in transmitter 252. This second set of MOSFETS is driven by a logic signal such that the voltage applied to the transducer is not a square wave but rather a generates (when driven in the appropriate sequence with the MOSFETS from transmitter 250) a crude representation of a Gaussian pulse shape which more closely matches the impulse response of the transducer 202. This additional complexity allows the transducer to be driven with less distortion and can improve imaging performance (axial resolution).

Another alternative transmitter 254 is shown in FIG. 11B, where a logic signal drives a digital to analog converter and is then fed to a linear amplifier and ultimately the transducer 202. The arrangement results in the highest imaging quality by driving the transducer 202 with a pulse shape matching its impulse response. This matching pulse shape is accomplished with a data sequence converted to an analog voltage via a Digital to Analog Converter (DAC) having a Gaussian pulse shape, which is then fed to the linear amplifier powered by the +/−150V rails. This is the least efficient solution in terms of power consumption but provides the optimum pulse shape.

By using one of the transmitters 250, 252, or 254 described above the Pulser/Receiver 204 generates a voltage pulse which is applied to the transducer 202. The pulses are typically within the range from about 2 to about 30 MHz and cause the transducer 202 to resonate at the applied frequency generating sound (acoustic) waves (beam 206) that are transmitted into the tissue 208. Depending on the constituents of the tissue 208 echoes or return signals are received by the transducer 202. These echoes are reflections of the sound (acoustic) wave the transducer 202 originally propagated. The return signals are transmitted back to and are received by the Pulser/Receiver 204. To protect the sensitive receiver front-end from the high voltage excitation pulse a Transmit/Receive switch (not shown) may be used. This is commonly implemented by a group of four diodes and may be integrated into transmitter integrated circuits (ICs) or is available as a stand-alone IC dedicated to this function. After passing through the Transmit/Receive switch, the return signals are then passed through a gain control module 212. To eliminate stray electrical noise, a band-pass filter (not shown) may be employed between the Pulser/Receiver 204 and the gain control module 212. The band pass filter may have a pass band that includes the transducer center frequency as well as, potentially, the lower −6 dB band edge where Doppler color flow imaging may be conducted.

In the gain control module 212 low noise amplification is undertaken to amplify the return signals and to minimize the noise associated with the return signal. As will be appreciated, return signals that are received later in time (i.e., which have traveled to a greater depth before returning) will be attenuated and associated with more noise. Thus a low noise amplifier may be the first active element in the receive signal chain. The low noise amplifier may also contain a provision to match its input impedance to the source impedance of the transducer plus the series impedance of the Transmit/Receive switch. Gain control module 212 may also perform variable gain amplification to account for return signal attenuation over time. The result of this attenuation is that echos which are received later in time (e.g., from deeper within the tissue) will require a greater gain to be applied to them than echos from tissues at a lesser depth. Thus, a variable gain amplifier adjusts the gain of the amplification applied to the return signals over time. A ramped gain curve is applied to maintain the echo amplitude within a digitizer range over the entire imaging depth. Thus the variable gain amplification aspects of the gain control module 212 can be controlled by a ramp module 214 which includes an adjustable voltage ramp which varies its voltage over time. This variable voltage is applied to the variable gain amplifier in gain control module 212 to adjust the gain on the variable gain amplifier. The typical attenuation of a signal passing through tissue of the body is approximately 0.5 db/cm/MHz. The controllable range typically spans 50 dB of gain. As a result, the ramp module varies its voltage, and therewith the gain of the variable gain amplifier of the gain control module 212 to compensate for this attenuation.

Figure 12:
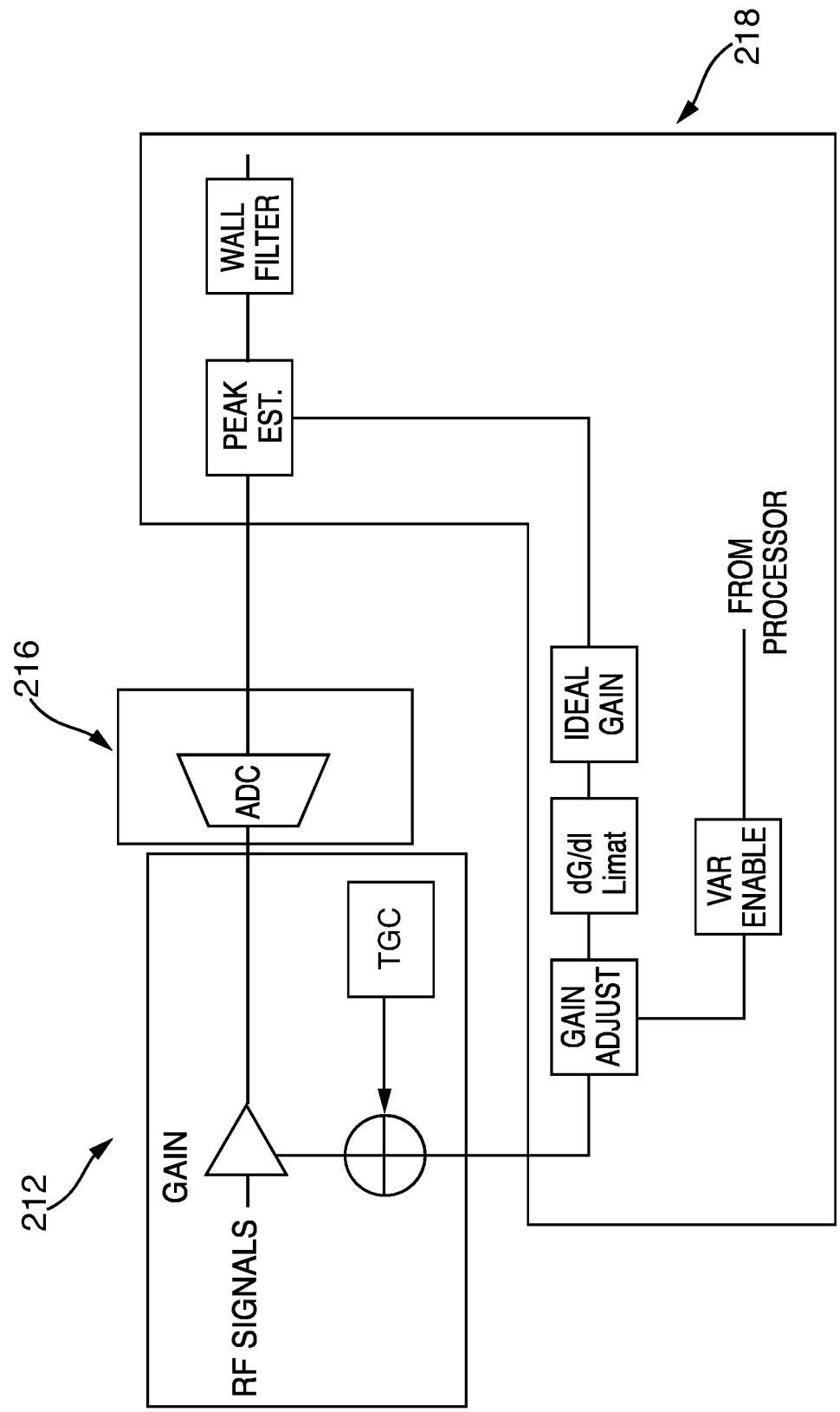
FIG. 12 is a schematic of a feedback loop for gain control according to one illustrative embodiment of the present disclosure.

Another aspect of the gain control module 212 is shown in FIG. 12, where a gain feedback loop is depicted. The feedback loop exist from the signal processor 218 (described below) controlling the variable gain amplification (described above) based on the average signal level measured at the Analog to Digital Converter (ADC) 216. As described above, predictive ramp (time gain control or TGC) is applied to the signals returned to the Pulser/Receiver 204. The TGC is based on average tissue attenuation and imaging depth. According to the feedback loop depicted in FIG. 12, the TGC value is summed with an additional control signal (gain adjust) from the signal processor 218 via a digital to analog converter. This summed gain value seeks to adjust the gain on the variable gain amplifier to maximize the dynamic range of the ADC 216.

The amplified and gain controlled signal from the gain controller 212 is then sampled in a ADC 216. The A/D may have 10, 12, 14 or 16 bits and certain embodiments of the present disclosure may benefit from using a higher dynamic range A/D converter to achieve more resolution in the quiet part of the image (anechoic spaces). The ADC produces a digital output representative of the return signals. This digitized output is then transformed via signal processing in a signal processor 218.

An alternative approach to sampling is synchronous sampling. In synchronous sampling, the RF wave is sampled at exactly 4 times the carrier frequency using a sampling clock which is phase coherent with the signal used to generate the transmit pulses. Thus if the transmit pulse is a burst of 10 MHz, the A/D converter samples the returning echoes at 40 MHz phase synchronous with the transmit clock. The resulting data can be directly converted to I,Q demodulated data in a very efficient manner in the FPGA (as will be discussed below). This technique is known as Quadrature Sampling IQ Demodulation.

In the signal processor 218, the digital output is passed through a digital band-pass filter to remove unwanted noise and harmonics. The digital filtering employs digital domain low pass filtering of the RF or display data to optimize the image in a more subjective manner. Further, high pass filtering including clutter filtering or Wall filtering may also be undertaken. A Wall filter is a fundamental component of a properly functioning Color Flow (Doppler) Imaging system. In addition to Doppler shift due to blood flow, any motion of the tissue relative to the transducer will also appear as a small frequency shift from the fundamental. This is referred to as clutter and is rejected via a high-pass filter with a very steep transition. The cutoff frequency is usually in the range from 100-500 Hz. Next the filtered digital output is rectified to identify the magnitude of the digital output over time. This magnitude data can then be be converted into a display of the return vs. depth as shown in one exemplary display 220.

As part of the signal processor 218 the signal is demodulated. The relevant tissue structure information is contained within the envelope of the returned RF signal. Demodulation removes the fundamental or carrier signal but preserves amplitude and phase information through time. The phase information is important for Doppler signal recovery so the demodulation scheme will seek to calculate I (in phase) and Q (quadrature) components. This may be achieved by active mixing of the RF with a synchronous sin and cosine version of the transmit clock or by quadrature sampling (described above).

Decimation is another aspect of the signal processing performed in the signal processor 218 and is employed where more data is captured in a given time frame than is in excess of that required to generate a useable image. The unnecessary data is either simply discarded (periodically described by a decimation factor) or is averaged in some way over successive pulse echo cycles before the data is passed to the next stage.

Once the signal is processed, it may be displayed. FIG. 10 shows an exemplary display 220 representing the return signal of a sound wave directed at the tissue 208 and traversing fluid filled lumen 210. As noted above, fluids within the body tend to be less echoic than the tissue through which they are flowing, and particularly the boundary layers of the tissue through which the fluids are flowing. As a result, when a sound wave passes through a fluid filled lumen 210, there are spikes of return representing the walls of the lumen and essentially very little return signal received (a quiet zone) from the fluid itself.

Figure 13:
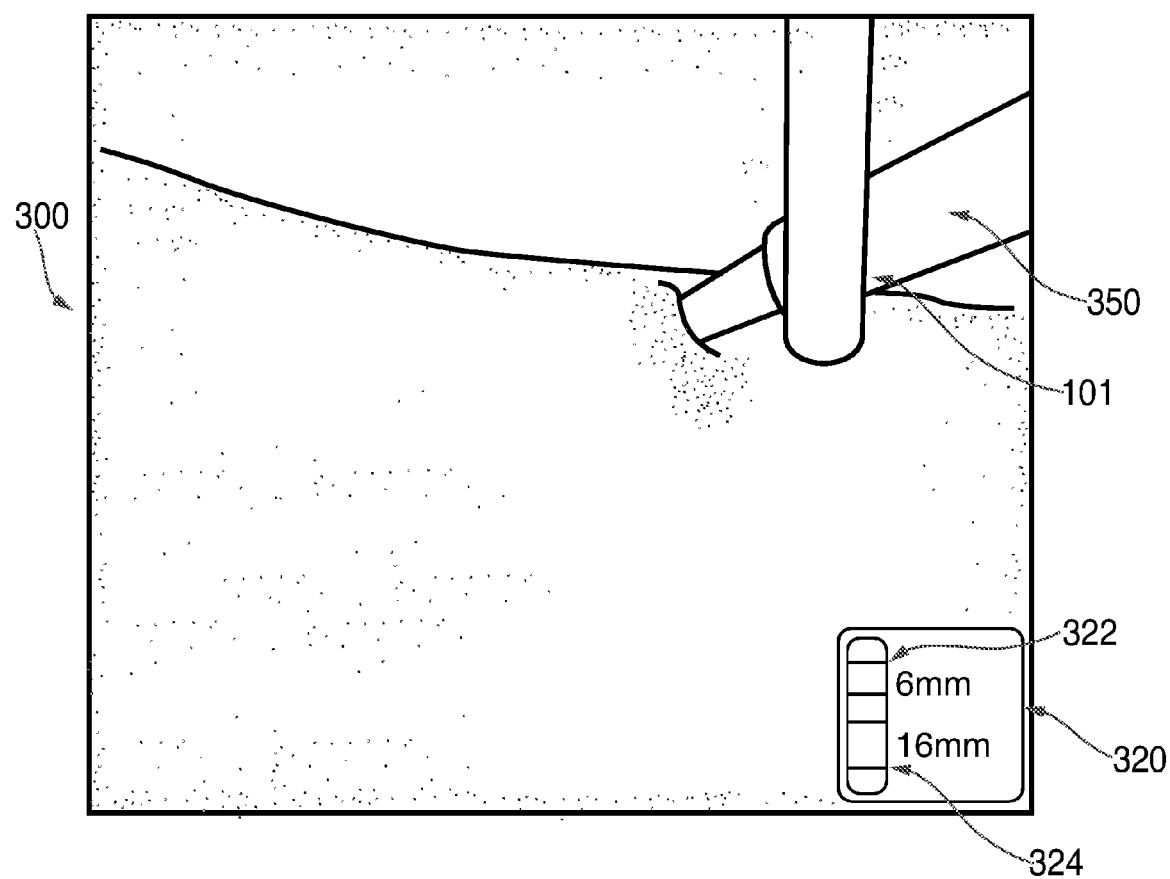
FIG. 13 is a composite optical image and "visual ruler" according to one illustrative embodiment of the present disclosure.

While the exemplary display 220 may be somewhat difficult for a surgeon or medical professional to analyze while performing an operation, the data that is represented there is very useful to know and can be further processed and incorporated into the optical display 300 (e.g., from a laparoscope) as depicted in FIG. 13. The optical display 300 depicts an image from a laparoscope of tissue within a human body. As shown in the optical display 300 a laparoscopic grasper 350 is grasping tissue and an ultrasound probe 101 is imaging tissue. The ultrasound probe 101 is connected to ultrasound processing components such as that described above with respect to FIG. 10.

In FIG. 13 the digitized, filtered, rectified, and display converted data is further processed to produce a visual ruler 320. The visual ruler is an alternative display of the same type of information presented in exemplary display 220. In interpreting the visual ruler 320 a surgeon will understand that in-line with the distal end of the ultrasound probe 352 and at a depth centered on about 6 mm is a lumen filled with fluid. This is represented by a first band 322 on the visual ruler 320. If, as shown in FIG. 13, a second fluid filled lumen is within the imaging scope of the ultrasound probe 101 a second band 324 can also be displayed in the visual ruler with the center of its depth indicated. The first band 322 identifies the location of lumen 110, and the second band 324 identifies the location of lumen 114. Moreover, as will be discussed in greater detail below Doppler modes may be employed to distinguish the type of these lumen (e.g., blood vessels, or other lumen) and if blood vessels the relative direction of blood flow. As a result of these further processing steps, the visual ruler 320 may be colored with for example a detected ureter being colored yellow and a detected blood vessel colored red or blue depending on direction of flow. As shown in FIG. 13, these different colors are shown by different types of cross-hatching in bands 322 and 324 respectively. Moreover, one or more audible, visual, or tactile alarms could be incorporated into the ultrasound probe 101 or display to alert the surgeon of proximity to critical structures such as the ureter or a blood vessel.

As a result of combination of the surgeons own knowledge of the anatomical structures currently in view through the laparoscope (e.g., the optical display 300) and the information provided via ultrasound probe 101 (e.g., the visual ruler 320) to identify with more clarity the location of various lumen, the surgeon has greater confidence in performing surgery. For example, using the visual ruler 320, a surgeon performing resection of tissue in the proximity of the ultrasound probe 101 in FIG. 13 would understand that resection of 1-2 mm can be undertaken without issue but to cut further may lead to severing the lumen centered at 6 mm of depth below the tissue surface. Moreover, by moving the ultrasound probe 101 and imaging in several locations the approximate path of the lumen can be determined with reference to the tissue currently before the surgeon. Thus, the macro shape and position of sub-surface structures can be presented to the surgeon without the unnecessary cognitive burden imposed by the need to mentally process a full-resolution ultrasound images on a separate display.

Though shown in FIG. 13 as having the ultrasound probe 101 separately inserted into the patient, those of skill in the art will recognize the benefits of incorporating the ultrasound probe 101 into the laparoscopic grasper 350 (or an electrosurgical instrument 10 as described above with respect to FIGS. 4A-4D). Not only would such an embodiment incorporation eliminate the need for a second instrument within the patient, but the data provided to the surgeon is then directly correlated to the movements of the laparoscopic grasper 350 within which the ultrasound probe is incorporated easing the cognitive burden on the surgeon to appreciate what the data is telling him or her with respect to the movements of the surgical instrument. Further, if incorporated into a laparoscopic grasper 350, the proximity alarm features discussed above can include one or more interlocks to prevent the grasping or dissection of tissue including the critical structures such as the ureter or blood vessels.

Regardless of whether incorporated into the laparoscopic grasper 350 or embodied in a separate ultrasound probe 101, the system described herein benefits from the direct contact with soft tissue within the body. Without the need to image through skin and the abdominal wall, higher frequency transducers can be employed to create image vectors with much greater resolution in the axial direction.

Because the ultrasound imaging data is provided and processed in near real-time the visual ruler 320 can provide active data. That is, the sizes of the lumens represented by the first band 322 and the second band 324 can be shown changing in diameter or pulsing. The pulsing represents an actual change the diameter of the lumen for example as it expands and contracts from heart beat pulses or in the case of a ureter due to the peristaltic waves which move urine from the kidneys to the bladder. Particularly in the case of the ureter, but as may be seen in other lumen such as the gall or bile ducts the diameter of the lumen can be perceived by the ultrasound probe 101 and the visual ruler 320 to disappear. This is due in part to the peristaltic muscle movements that force fluids through the lumen. At times where the muscles immediately in the imaging beam of the ultrasound beam are contracting and forcing fluid down the lumen, the lumen walls can be forced into contact with one another. The muscle movement forces the fluid out of the imaged area thus there is no portion of the return signal which has the quiet zone (i.e., is non-echoic) as shown in FIG. 9. When the returned image data is processed, the result is that the lumen is perceived to disappear as the signal returned from the lumen walls is similar to that of the surrounding tissue and is more difficult to determine in the absence of the fluid. However, this disappearing state is generally only of short duration as at least some fluid tends to flow into the lumen as soon as the muscles relax. As will be appreciated by those of skill in the art, the use of M-mode ultrasound is particularly useful in this embodiment as it provides a movie like image showing changes in the image over time (e.g., the presence and absence of an anechoic area) which coincides with the peristalsis. The identification of an lumen undergoing peristalsis assists in confirming the diagnosis and identification of the lumen.

Figure 14:
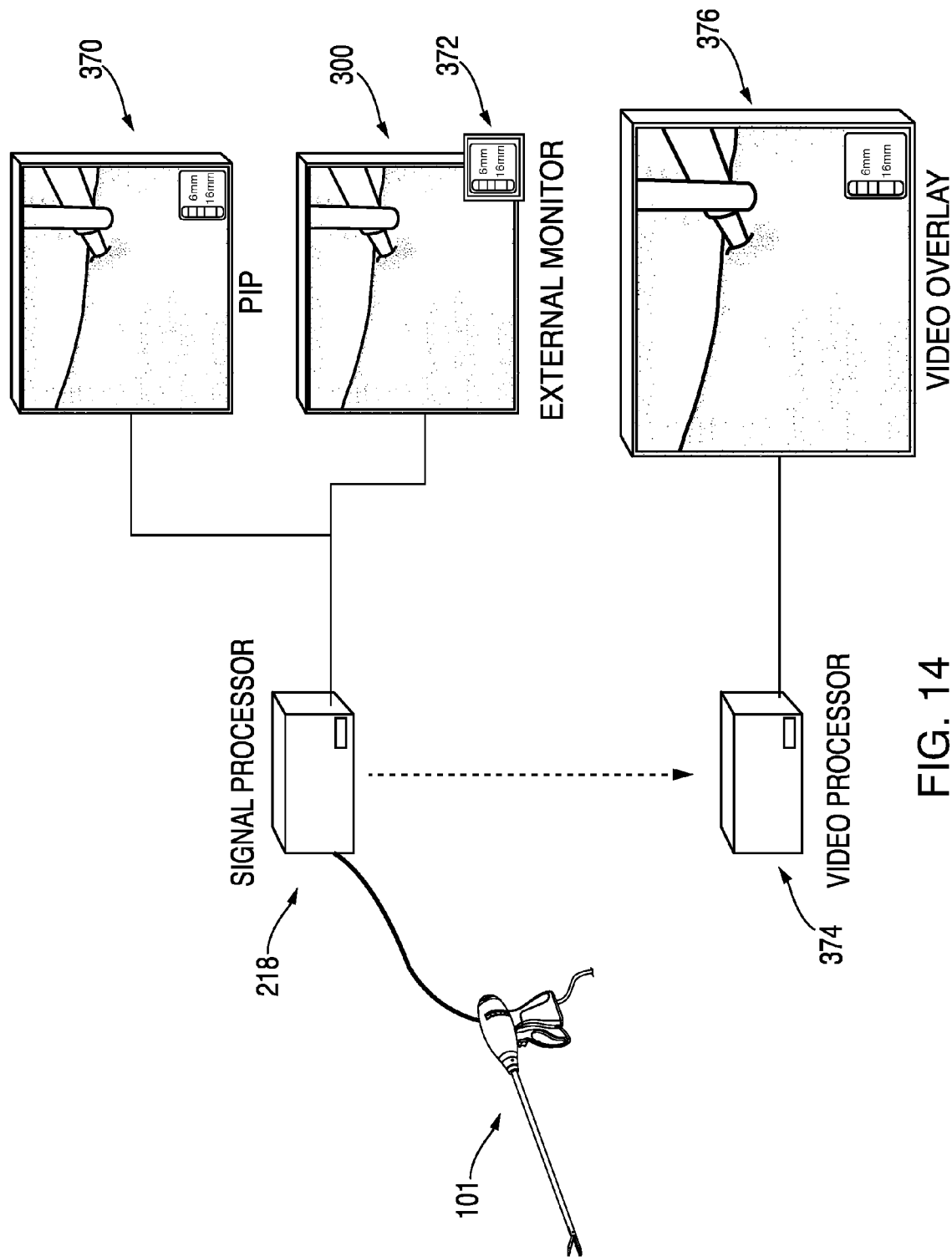
FIG. 14 is a schematic of three different image display arrangements according to illustrative embodiments of the present disclosure.

FIG. 14 depicts three different methods in which the visual ruler 320 can be employed with the optical display 300. As shown in FIG. 14 the probe 101, sends returned ultrasound signals to the signal processor 218, which processes the returned signal as discussed above. From there, three different types of displays are contemplated. The first display 370 uses Picture-in-Picture technology. The signal processor 218 outputs a video signal that is likely full frame, standard definition video. This video stream is fed to the picture in picture port available on all major laparoscopic video systems. The PIP function is enabled which places the ultrasound graphic display directly on the monitor in real-time occupying approximately 15-20% of the user's field of view, for example set in the lower right or left corner. The location and size is configurable on some systems, depending on the manufacturer of the monitor.

Alternatively, the display 372 is an entirely separate monitor, for example mounted on an IV pole. A separate display output connects to a dedicated display 372 in addition to the optical display 300 described above. This concept adds to the signal processing box a dedicated display 372 which only shows the ultrasound graphic data. This can be positioned as necessary in the OR (i.e. in front of and just to the side of the primary laparoscopic display). Such a configuration may be particularly useful when incorporating the display 372 with existing OR infrastructure.

A third option for the display would be to incorporate the visual ruler 320 into a graphic user interface of an advanced electrosurgical generator. Such an approach simplifies the cabling as the ultrasound data and additional functions supported by the disposable device can be cabled to the same location and potentially integrated into the same connector. Such an implementation is described below with respect to a robotic arrangement.

Yet a further option involves a video processor 374. In such an implementation the laparoscopic video stream is intercepted and merged with the ultrasound output from the signal processor 218. This configuration allows more control over the user interface. There are several advantages of such an implementation including that the display can be smaller than the fixed Picture in Picture window described above, and thus so can present only the graphic required without occupying unnecessary space on the primary field of view. Similarly, the display can be only momentarily present under user control when needed and can auto-hide when not in use.

Figure 16:
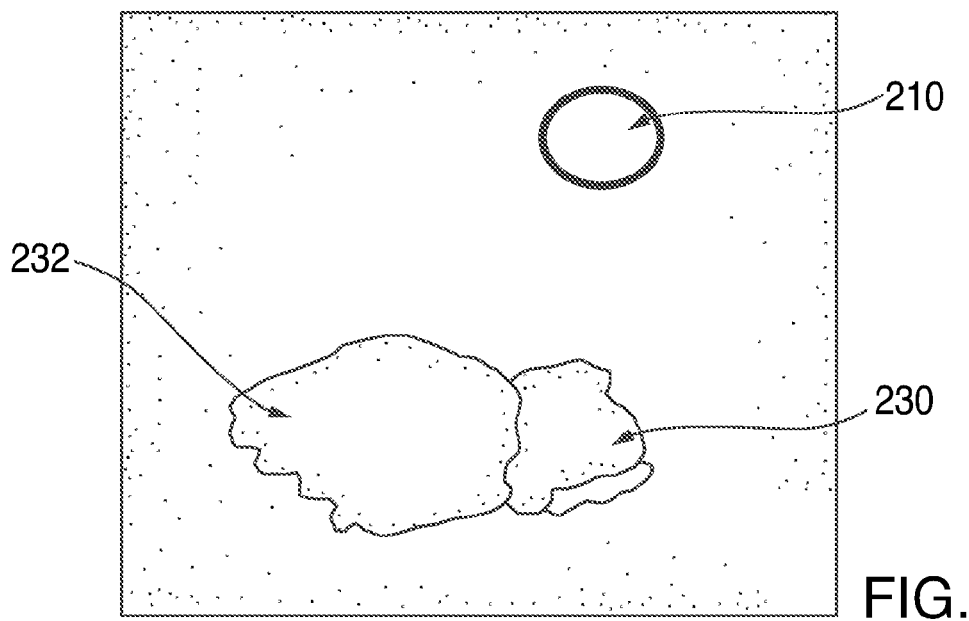
FIG. 16 is an ultrasound image based on the interrogation of FIG. 14 according to the present disclosure.
Figure 17:
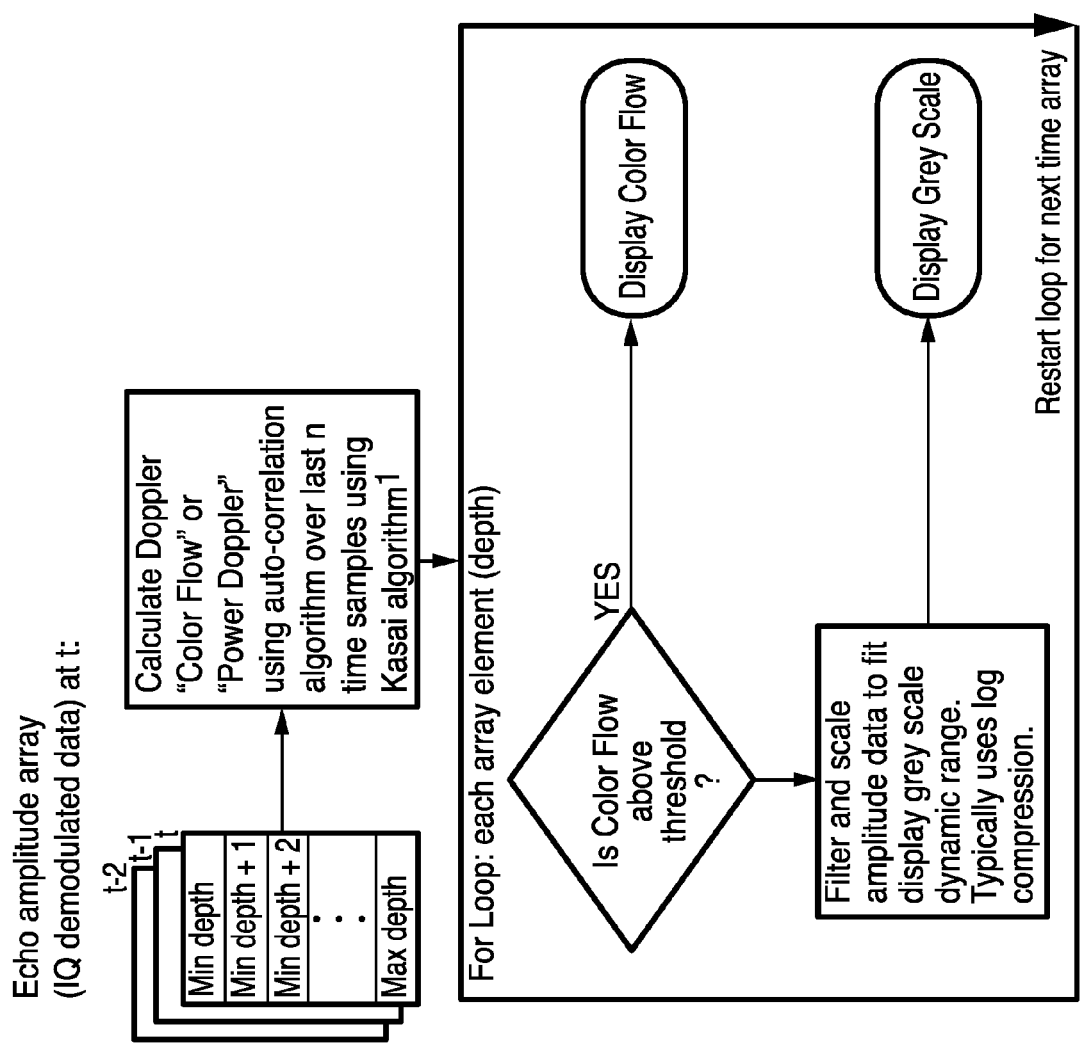
FIG. 17 is a flow chart of the image processing to produce a Doppler ultrasound image according to one illustrative embodiment of the present disclosure.

A further embodiment involves the processing of the single vector of ultrasound energy, and its return signals, in time and space as the user moves the transducer relative to the tissue as shown in FIGS. 16 and 17. A 2-D cross section perpendicular to the visual plane with great depth detail can be created by the user sweeping a linear path with the device thus approximating the image from a traditional laparoscopic ultrasound transducer.

Figure 15:
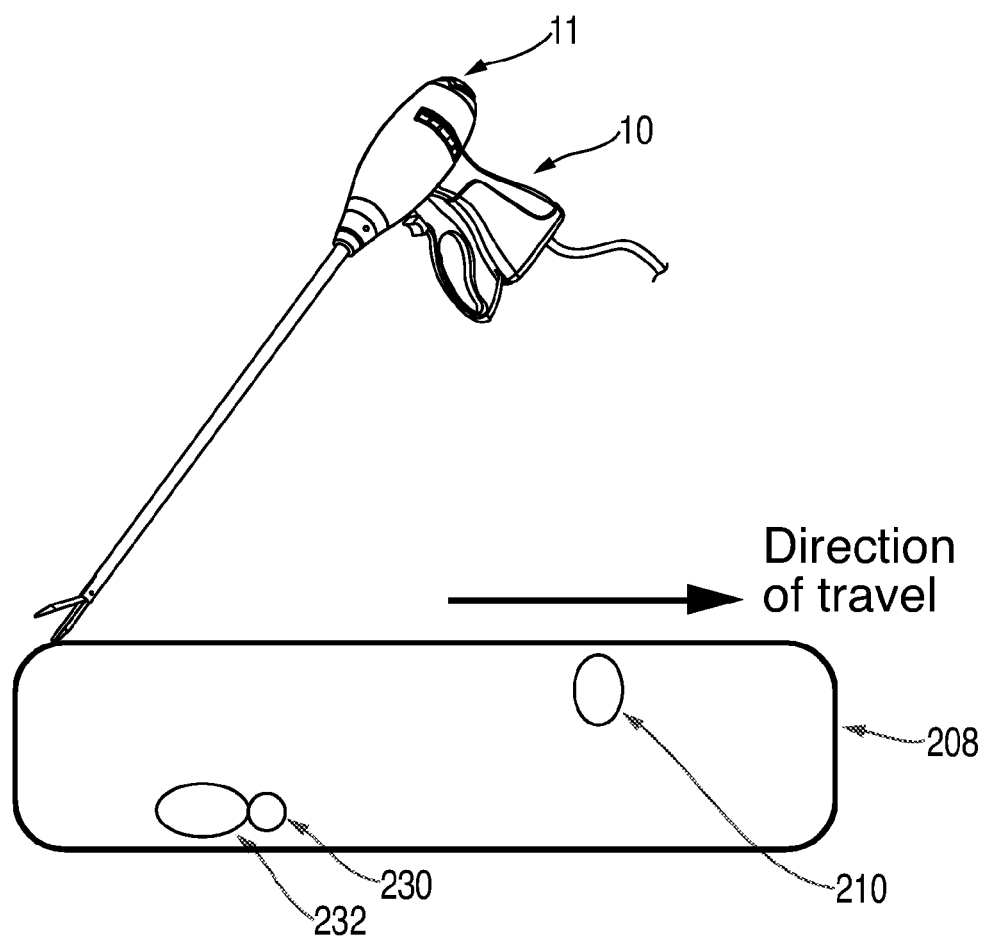
FIG. 15 is a schematic of an electrosurgical instrument with ultrasound probe interrogating tissue according to one illustrative embodiment of the present disclosure.

This embodiment of the present disclosure is directed to a method of generating a 2D image from a single element device wherein the user sweeps device to create 2D image perpendicular to visual plane. A 2D image is created by sweeping 1D transducer and closely monitoring the returns over time to sense changes in the returns which correlate to changes in the structure. In one embodiment, as shown in FIG. 15, a user presses a button 11 on a surgical instrument 10 and begins to sweep in one direction. The sweep time is limited to some fixed time, for example 3 seconds. This may be adjustable from 1-10 seconds by the user, when for example a user wishes to view a larger area. The result of scanning the tissue 208 in FIG. 15 is an image such as that shown in FIG. 16. In both FIGS. 16 and 17 the ureter 210 and two blood vessels 230 and 232 are identified by the ultrasound imaging. Each successive sweep of the tissue 210 can produce an image. Thus the surgeon can compare the image of the underlying tissue with the tissue presented by an optical image produced by a laparoscope to determine where critical structures such as a ureter or blood vessels are so that they can be avoided or targeted as the case may be.

In the example described above with respect to FIGS. 15 and 16, the fluid-filled lumens can be identified in the A-mode ultrasound data as the regions of low backscatter. If however, B-mode is employed, or A-mode samples are converted to B-mode, then further details of the underlying tissues can be resolved and displayed. As noted above, Doppler, Color Doppler, and Power Doppler and Pulsed Wave Doppler can be used to detect the phase between the ultrasound signals propagated with that returned. Based on the direction of the phase shift and the magnitude of the phase shift flows of certain fluids, and the relative direction of flow can be determined. The use of Pulsed Wave Doppler is well known in the ultrasound imaging art, accordingly detailed description is omitted here.

In FIGS. 15 and 16 two blood vessels are depicted 230 and 232 along with another lumen 206, which may be, for example, a ureter. As shown in FIGS. 15 and 16 three different shadings or colors are employed to indicate velocity of flow and or relative direction. The flow of fluids in the lumens 230 and 232 which are for example blood vessels and therefore are moving at a relatively high velocity can be resolved using Doppler display processing as shown in FIG. 17.

In FIG. 17, a series of signals are propagated from an ultrasound transducer 202 at time intervals t-n through t. At each of these time intervals echo returns for depths ranging from a Min depth to Max Depth are received and stored. A phase shift of the echo return as compared to the propagated signal can be calculated for the time intervals and at each depth. This may be done using an auto-correlation algorithm such as the Kasai algorithm for a number of samples n. One exemplary correlation algorithm is that developed by Kasai. (See e.g., C. Kasai et al, *Real-time two-dimensional blood flow imaging using an autocorrelation technique*, IEEE Transactions Sonics. Ultrasound. 32 458-464 (1985)). This is a common method to detect the presence of moving structure or blood flow at points along the ultrasonic beam. The autocorrelation algorithm compares I and Q components of the RF signal from the present and prior (1st lag) digitized echo lines to create an estimate of the mean Doppler frequency shift. This technique is computationally efficient as compared with an FFT-based technique to isolate the same mean frequency shift. Based on the correlation a determination can be made as to whether the phase shift is greater than a threshold value, if yes then a color will be displayed in that portion of the ultrasound image possessing a phase shift greater than the threshold magnitude, for example the color red may be displayed. For the remainder of the display grey scale may be used as would be otherwise expected. In instances where there are two or more regions of the ultrasound image displaying phase shifts then two or more regions may be colored. In the event the magnitudes of the phase shift of these two areas are in excess of the threshold but the directions of the phase shift are different, then different colors may be employed since the different directions of the phase shift represent fluid flowing in different directions.

Figure 18:
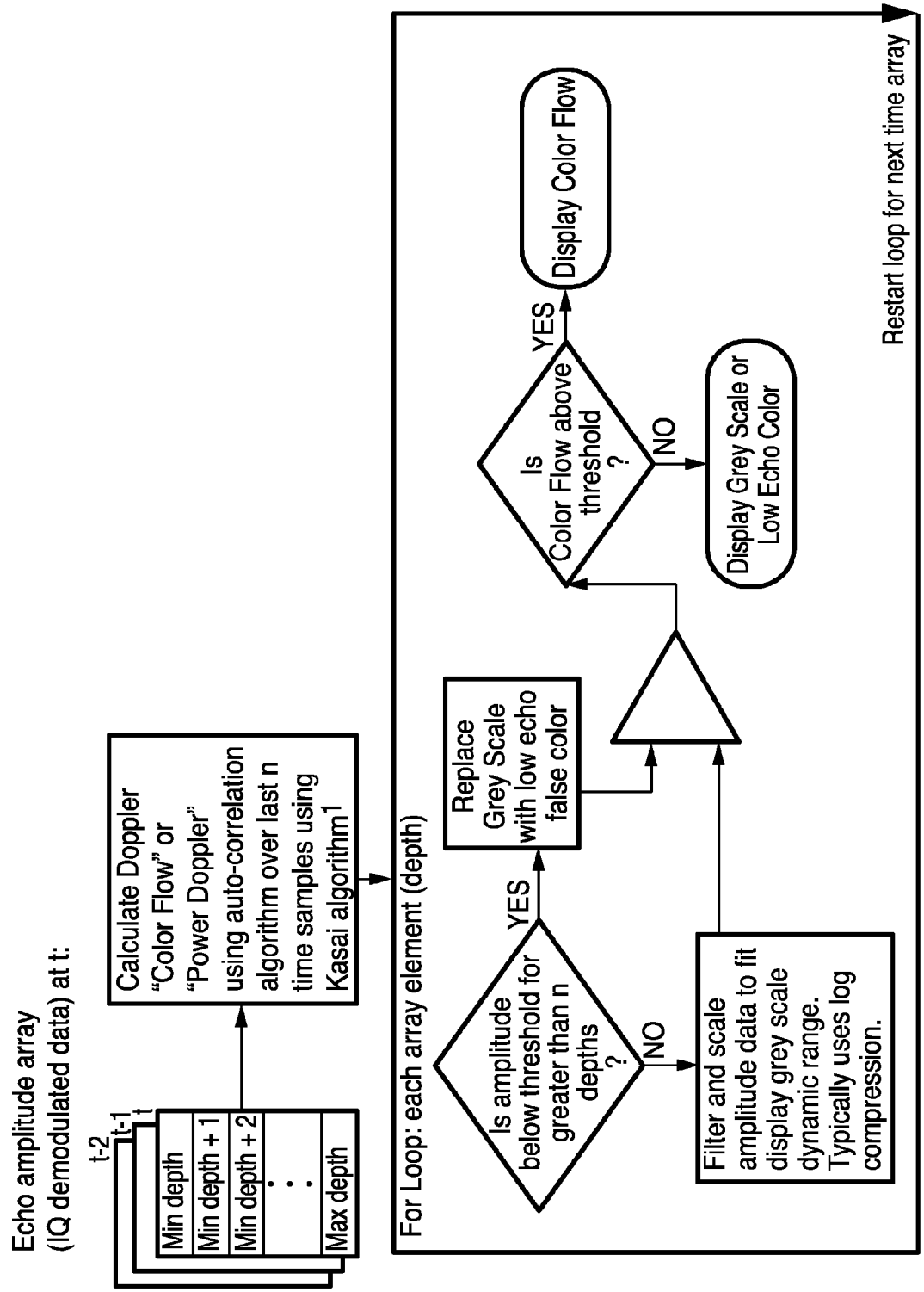
FIG. 18 is a flow chart of the alternative processing to produce a Doppler ultrasound image according to one illustrative embodiment of the present disclosure.

FIG. 18 depicts a variation of that shown in FIG. 17. In FIG. 18 rather than taking the Doppler correlated data and first determining whether the phase shift is above a predetermined threshold as in FIG. 17, the first inquiry is whether some portion of the return signal has a amplitude of less than a predetermined value for greater than some distance (n depths). If the answer to this inquiry is yes, those portions of the ultrasound image will be replaced with a low echo false color. Effectively, this first step is determining which portions of the ultrasound image are fluid filled lumens (i.e., those that are low echoic or non-echoic). Once these have been determined, the remainder of the image is left as grey scale as is customary in ultrasound imaging. The entire ultrasound image, both those portions that have been replaced with a low echo false color and the portions that are left in grey scale are analyzed again. This time the magnitude of the phase shift is analyzed to determine if the velocity of the fluid exceeds a certain threshold. If yes, then those portions of the ultrasound image are colored as described above with respect to FIG. 17, and again differences in the direction of the phase shift may be considered to reveal two or more lumens with fluid flowing in different directions. These are represented by different colors. Any portion of the ultrasound image which does not demonstrate a phase shift in excess of the threshold is left in either grey scale or with the low echo color (for example yellow) applied in the preceding step. The use of this two step process enables the user to determine the location of lumens within the body and have their identity further clarified with respect to whether they are blood vessels or some other lumen like the ureter. Moreover the use of color makes the distinction between a blood vessel and some other lumen immediately clear to the surgeon.

As noted above in the description of the visual ruler 320 embodiment, Doppler may be employed in that embodiment to distinguish between the first band 322 and the second band 324. This may be accomplished using the processing described with respect to FIG. 18. As a result of the combined processing, the visual ruler 320 displays not only a lumen such as the ureter 206, but also blood vessels 230 and 322 (when they are in the imaging vector of the transducer 102, 202 and provide the surgeon not only depth and location information but also some indication of identification of the lumen being imaged.

In the embodiments described above with respect to FIGS. 15 and 16, the ultrasound imaging transducer 102, 202 must be drawn across the tissue in order to image the underlying structure. The linear sweep by the user coincides with a draw function on screen to convert the one dimensional return signal into a two dimensional cross-section image that can be displayed. While an acceptable result can be achieved without further input to the system, either through training of medical professionals or through putting limits on the manner in which the device may be used there are at least two additional inputs to the system which provide data that will make the device easier to use and provide better results. The two data inputs are sweep direction and sweep speed.

As will be readily understood, without providing data indicating the direction of travel, a system employing the sweeping method described herein may be limited to a single direction of travel to ensure acceptable results. As a result, if the surgeon sweeps the surgical instrument or ultrasound probe in the opposite direction the 2D image generated will be reversed in the horizontal direction resulting in a confusing display for the surgeon, a situation which should be avoided if possible.

As to sweep speed, without knowledge of the velocity of the transducer 202 over tissue, the generated 2D image may be distorted in the horizontal direction. i.e. if the user sweeps at a pace either faster or slower than optimal for the processing system the, circular lumens in cross-section will appear ovalized or stretched horizontally or they may be missed entirely. As a result of these limits, further inputs are useful in expanding the capabilities and heightening the quality of the results.

Figure 19B:
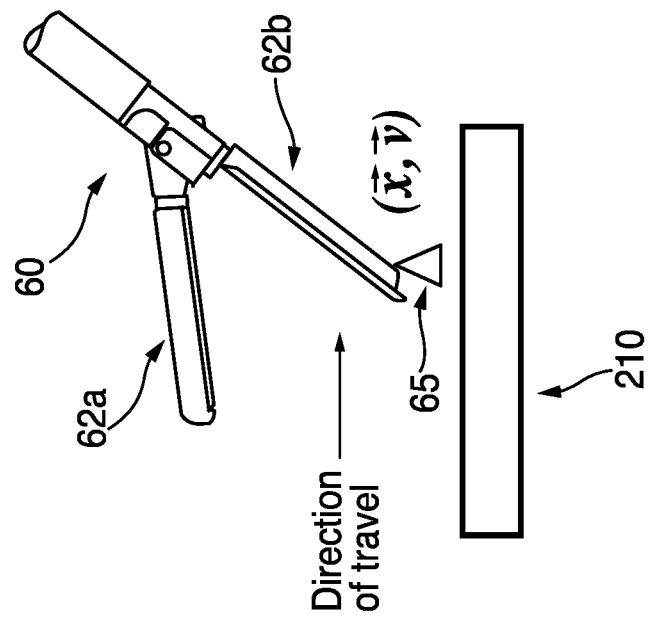
FIG. 19B is a profile view of a surgical instrument employing an optical motion sensor to determine speed and direction according to one illustrative embodiment of the present disclosure.
Figure 19A:
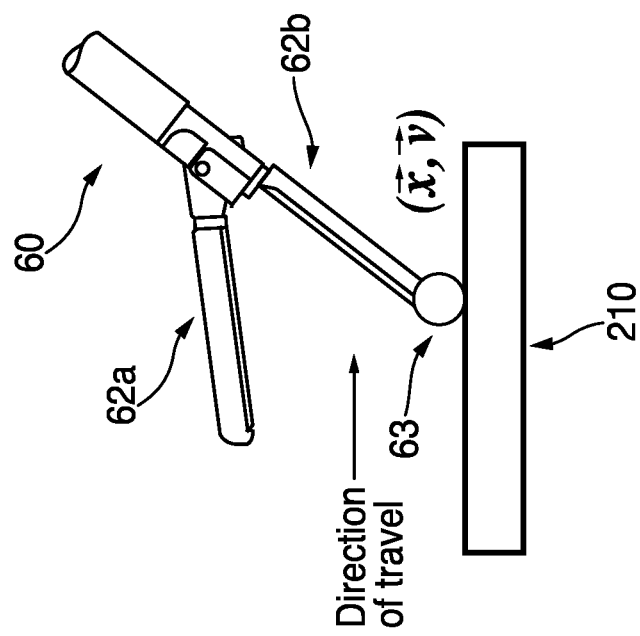
FIG. 19A is a profile view of a distal portion of a surgical instrument employing a track ball to determine speed and direction according to one illustrative embodiment of the present disclosure.

According to one embodiment of the present disclosure, location, speed, and direction data can be provided using a track ball configuration as shown in FIG. 19A. FIG. 19A depicts and end effector 60 of a bipolar forceps. The fixed jaw 62*b* has a track ball 63 connected to its distal end. The track ball 63 is held in contact with the tissue to be imaged 210 and drawn across the tissue. By contacting the tissue 210, as the track ball 63 is drawn across the tissue it rolls. Analysis of the rolling of the track ball 63 allows for determination of direction, based on the direction the track ball 63 rolls, and the speed of travel can be determined based on rotational speed of the ball.

FIG. 19B depicts an alternative embodiment for determining speed and direction information of an end effector 60. The embodiment in FIG. 19B employs an optical motion sensor 65, similar to a modern computer mouse. The optical motion sensor transmits a light such as a laser against the tissue and based on the detected changes in light reflected from the tissue and received by a sensor on the end effector 60a determination can be made of both the direction of travel and the speed of the end effector 60. Using an optical motion sensor 65 has the advantages of eliminating moving parts and a resistance to fluids and tissues that could affect the performance of a track ball 63.

Figure 20B:
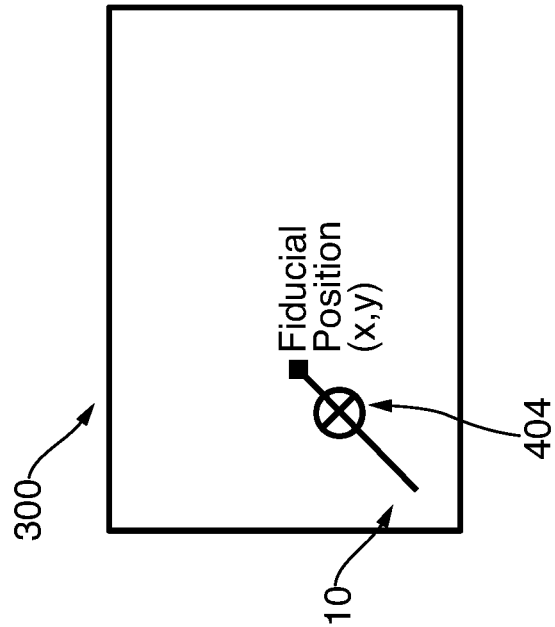
FIG. 20B is a graphical display of a surgical instrument employing an active tracking device according to one illustrative embodiment of the present disclosure.
Figure 20A:
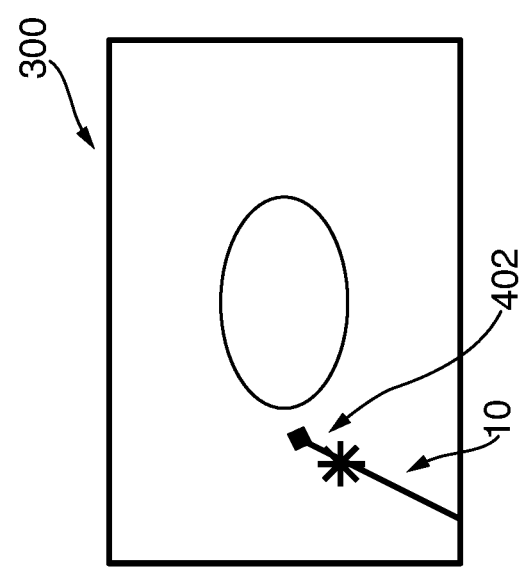
FIG. 20A is an optical display of a surgical instrument employing an active tracking device according to one illustrative embodiment of the present disclosure.

A further alternative embodiment can be seen in FIGS. 20A and 20B in which a fiducial is employed with the surgical instrument. FIG. 20A shows an optical display 300 such as used in connection with a laparoscope or other camera for displaying images of tissue within the body. On the optical display is an image of the surgical field in which there is an electrosurgical instrument 10 or ultrasound probe 101, the electrosurgical instrument 10 includes an active fiducial device 402 such as a strobe light. Using the optical imaging components (e.g., a laparoscope) the fiducial 402 can be tracked as it traverses the visual plane. This tracking in the visual plane resolves X and Y data relating to the position of the fiducial device 402 within that plane. Further, depth of Z direction data can be determined based on size or brightness of the fiducial device 402 in the optical display. Alternatively, the Z-axis depth can also be ascertained by employing a plurality of strobes along the shaft at varied spacing at each depth along the shaft. FIG. 20B depicts a graphical representation of the electrosurgical instrument 10 as it might appear in a graphic overlay on display 300.

An alternative, not shown, is to employ a passive fiducial marker is placed on the shaft of the surgical instrument 10. Again by tracking the position and size of the passive fiducial marker the X, Y, and Z locations of the surgical instrument can be determined. Other types of passive fiducial markings may also be employed including the use of additional cameras and dots on a patch of material as is generally known in the art. By comparing the changes in location over time both speed and direction data of the electrosurgical instrument 10 can be calculated.

While the above described tracking embodiments are directed to internal tracking of an electrosurgical instrument 10, the present disclosure is not so limited and known external tracking systems may also be employed to track the absolute or relative position of an electrosurgical instrument 10 or probe 101. For example, the absolute position of an electro surgical instrument 102 may be determined using electromagnetic tracking. One known system for such electromagnetic tracking is the InstaTrack system developed by General Electric. Alternatively, the relative position of an ultrasound probe 101 or electrosurgical instrument 10 as compared to a laparoscope can be determined using an additional video camera and a patch of dots. Based on the change in image of the dots being imaged, the movements of the video camera, and therewith the instrument to which it is attached can be assessed and processed in comparison to the other instrument. Such video approaches are well known in the art and are used to register the position of one instrument vs. another (i.e., relative positioning) particularly for imaging purposes.

Figure 21:
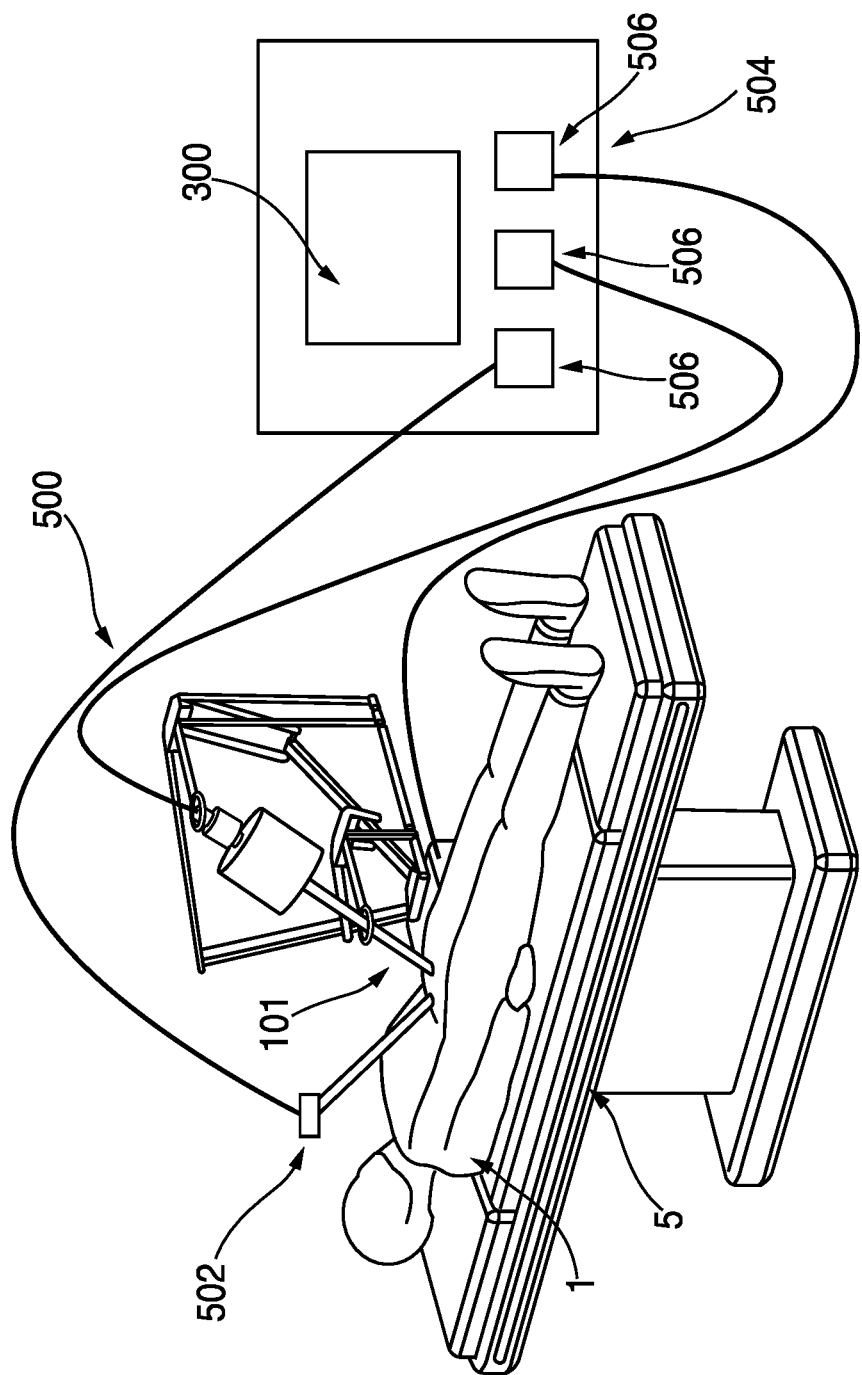
FIG. 21 is a perspective view of a robotic manipulator system according to one illustrative embodiment of the present disclosure.

Yet a further method of tracking the movements of an ultrasound imaging probe 101 or electrosurgical instrument 10 is through the use of one or more robotic manipulators 500 as shown in FIG. 21. As shown in FIG. 21 an ultrasound probe 101 may be mounted on or controlled as part of a robotic surgical system 500. As a result, the task of tracking the ultrasound probe 101 in space and time with respect to the patient 1, the operating table 5, or a laparoscope 502 (which may alternatively be mounted on and controlled by the robot manipulator 500) is accomplished in the robotic controller itself.

As shown in FIG. 21, the robotic manipulator 500 is connected to a controller 504 which controls the movement of the robot manipulator 500, provides energy to the ultrasound probe 101 and laparoscope 502, and if connected provides controlled electrosurgical energy for an electrosurgical instrument 10 (not shown). As shown, the controller 504 includes a display 300, and connection ports 506. Controller 504, through the connection ports 506 may provide the necessary power and algorithmic processing to produce laparoscopic images with the laparoscopic probe 502, produce the ultrasound images with the ultrasound probe 101 such that they can be both be displayed in real time on the display 300 (as described above), provide energy for one or more electrosurgical instruments 10, and control the movement of the robot manipulator 500.

By controlling the movements of the robot manipulator, the controller 504 is able to register both the absolute positions of devices under its control, and also the images displayed on the display, such that real time overlapping image data, for example an optical image overlaid with an ultrasound image can be displayed for use by the surgeon. As will be appreciated, such an arrangement also makes it possible to control the robot manipulator 500 remotely, such that the surgeon need not necessarily be in direct attendance with the patient 5.

The use of a robotic manipulator 500 eases the implementation of certain aspects of the present disclosure because the robotic manipulator 500 already possesses the requisite absolute and relative possession information of the implements under its control (e.g. ultrasound probe 202 and or laparoscope 502). This absolute and relative possession information may be accomplished through any number of registration and location detection mechanisms which are known in the art of robotic surgery. Indeed, under control of a robotic manipulator, the generated ultrasound images may have enhanced image quality due to the substantial elimination of and correction for variations in the transducer path as it is passed over the tissue it is imaging as compared to the surgeon held techniques described above.

A further embodiment of the present disclosure relates to the generation of overlays of the ultrasound imaging data onto the images generated by optical imaging techniques such as laparoscopy. Through the tracking methods described above, whether internal, external, robotic the collected location of the ultrasound probe can be detected and its movements tracked as the probe moves across the visual plane or image generated by the optical imaging device (e.g., laparoscope). By identifying the location of the ultrasound probe in space and time, the ultrasound images or data generated by the ultrasound probe can be registered with respect to the optical image. The result is a layer of ultrasound data that can be overlain the optical image to reveal to the surgeon in a single display image both the visible structures and the structures which reside beneath the surface of the visible structures, thus creating a simplified 2-D display of 3-D data.

Figure 22:
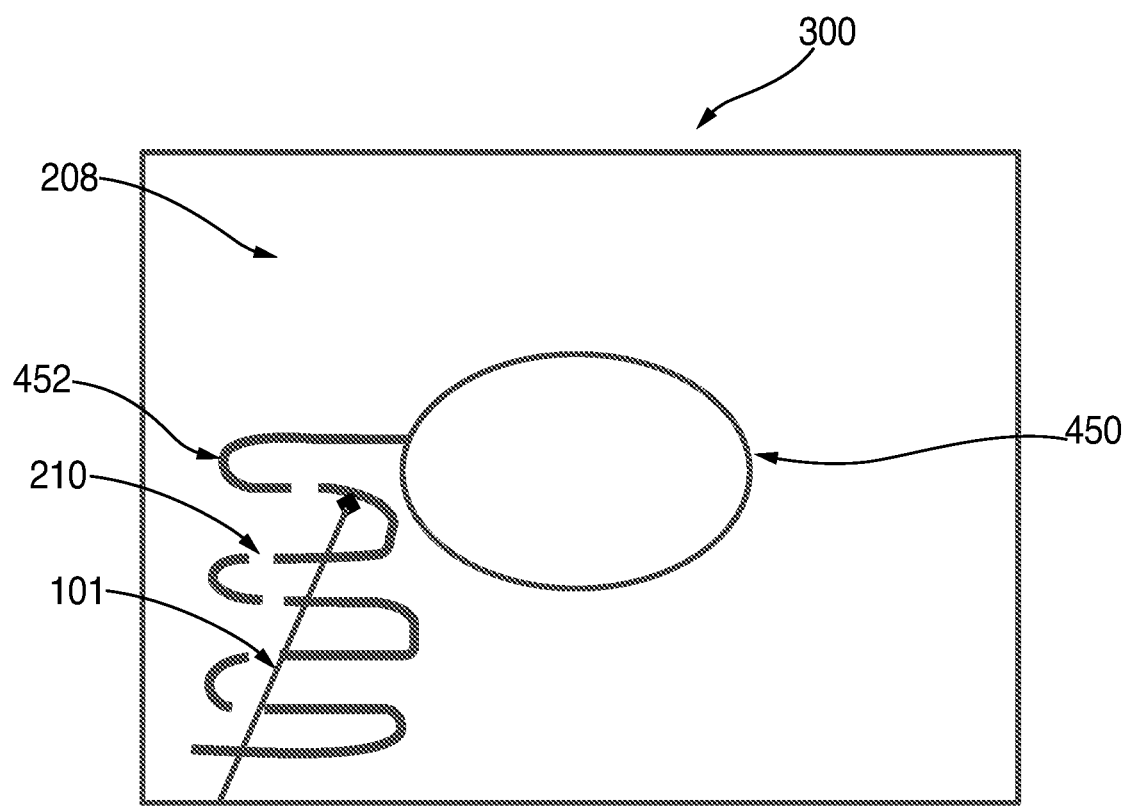
FIG. 22 is a representative display of a bladder and ureter according to one illustrative embodiment of the present disclosure.

As shown for example in FIG. 22, a 2-D map of structures can be created in the visual plane by the user sweeping an ultrasound probe 101 across the tissue surface 208. This map can then be overlain the laparoscopic image so that the structures detected by the ultrasound imaging are presented with reference to the structures that are visible in the optical imaging display, such as that from a laparoscope. Specifically, FIG. 22 depicts a single display 300 in which the bladder 450 is displayed through the use of an optical imaging device such as a laparoscope. In order to assist in the registration of the optical image and ultrasound images or data, it is sometimes desirable that the movement of the laparoscope or camera be limited, though as will be appreciated this impacts the surgeons ability the use the laparoscope over a wide range of areas. In some embodiments, the limitations on movement of the laparoscope for purposes of registration of ultrasound images or data can be temporary and selectable such that the limitations on movement are on present during that portion of the procedure where the surgeon requires the ultrasound imaging and/or registration with the optical imaging.

In the technique shown in FIG. 22, a surgeon moves the surgical instrument such as a ultrasound probe 101, or electrosurgical instrument 10, across the visual plane of the tissue 210 imaged by the optical imaging components. The visual plane is that plane displayed on the display 300. In one embodiment, when the ultrasound imaging features are turned on, the tracking features track and display the path of the ultrasound probe 101 across the visual plane, the path is shown in FIG. 22 as the sinusoidal line 452. The tracking and registration can be accomplished by one or more of the tracking techniques described above. Where a particular type of feature such as a fluid filled lumen is detected using the process described herein above, the image shown on display 300 is modified to depict that sensed structure. In FIG. 22, at points along the path 452 of the ultrasound probe 101, the ultrasound imaging system identifies portions of the ureter 210. Using similar techniques other lumens such as blood vessels could also be identified and as noted above using Doppler, a requisite color can be associated with the ureter or blood vessel to identify more specifically the detected lumen. Thus, using this technique, the surgeon is able to effective paint the location of a structure such as the ureter 210 onto an optical image in which the ureter would otherwise be hidden from view. This allows the surgeon to approximate the location of that structure and to avoid or treat that structure as necessary with greater confidence.

As can be appreciated the ultrasound imaging techniques and overlay creation techniques can also employ curve fitting and approximating techniques. Thus, when three or more instances of the structure are identified the display system could approximate likely locations of that structure between the definitively identified locations and effectively fit a curve between these locations. This may be done in the same color or in a different color as that used to identify exact locations of the structure. Using this technique the surgeon need only make a few quick passes over the structure to located and an approximation of that structure can be quickly resolved. As will be appreciated, the greater the number of precise locations of structure that are identified the greater confidence the surgeon can have in that approximation.

In a further embodiment of the present disclosure, the surgeon could effectively paint the entire visual plane with the ultrasound data such that any structure that is within the visual plane but beneath the surface of the tissue 208 is revealed to the surgeon. As can be appreciated, this technique reveals a great deal of information that may be unnecessary for the task at hand and may also clutter the optical image produced by the laparoscope or other camera. In such a system tracking data would be necessary to ensure that the visual plane had been completely pained by the ultrasound imaging probe and also to eliminate overlap in the generated ultrasound image/data associated overlapping movements of the ultrasound imaging probe.

A further embodiment of the present disclosure is directed to utilizing the above described ultrasound probe 101 to conduct in vivo quantitative ultrasound. Each of the ultrasound techniques described above rely at least in part on the concept of image segmentation. Image segmentation involves the process of joining individual pixels or sets of pixels (super pixels) into segments. These joined pixels and/or super pixels share certain visual characteristics. The goal of the segmentation is to simplify and to improve the ultrasound image making it easier to analyze. Often image segmentation is used to identify and locate a particular structure or boundaries between structures and represent these boundaries as continues lines or curves separating the structures.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. More particularly, certain aspects of each of the embodiments described herein may be utilized with aspect of other embodiments in various combination and sub-combinations without departing from the scope of the present disclosure.

We claim:

1. A method comprising:
   receiving ultrasound data from at least one ultrasound transducer;
   processing the ultrasound data to produce a graphical representation depicting echoic attributes of tissue substantially axially aligned with a transmission path of the at least one ultrasound transducer and the distance of at least one tissue type having different echoic attributes from surrounding tissue from a distal tip of a laparoscopic surgical instrument embodying the at least one ultrasound transducer; and
   outputting a signal for display of the graphical representation,
   wherein the graphical representation includes a real-time visual ruler displaying dynamically changing data corresponding to changing depictions of the graphical representation.

2. The method of claim 1, wherein the graphical representation depicts a location of one or more lumens in axial alignment with the transmission path of the at least one ultrasound transducer.

3. The method of claim 2, wherein the graphical representation depicts a lumen with flowing blood.

4. The method of claim 2, wherein the graphical representation depicts a fluid filled lumen.

5. The method of claim 2, wherein Doppler ultrasound identifies a direction of flow in the one or more lumens.

6. The method of claim 1, wherein the processing employs at least one of an A-mode,-B-mode, or M-mode ultrasound to generate the graphical representation.

7. The method of claim 1, wherein the at least one ultrasound transducer is integrated into the laparoscopic surgical instrument.

8. The method of claim 1, wherein the visual ruler provides a macro-shape and a position of one or more lumens in axial alignment with the transmission path of the at least one ultrasound transducer.

9. The method of claim 1, wherein the processing employs Color Doppler ultrasound.

10. The method of claim 1, wherein the processing employs Power Doppler ultrasound.

11. The method of claim 1, further comprising tracking the laparoscopic surgical instrument to determine location, speed, and direction data of the laparoscopic surgical instrument.

12. The method of claim 11, further comprising optically imaging a region of interest and outputting an optical image to a display.

13. The method of claim 12, further comprising processing the location, speed, and direction data of the laparoscopic surgical instrument and outputting to the display the visual ruler.

14. The method of claim 13, wherein an area of the visual ruler representing movement of the laparoscopic surgical instrument across the optical image is shown in a first color.

15. The method of claim 14, wherein an area of the visual ruler representing a detected fluid filled lumen is depicted in a second color.

16. The method of claim 1, further comprising displaying an ultrasound image depicting a cross-sectional view of tissue across which the laparoscopic surgical instrument has been drawn.

17. The method of claim 16, wherein the visual ruler is incorporated into a graphical user interface of an electrosurgical generator.

18. The method of claim 17, wherein dynamically changing the data relates to pulsing of one or more lumens depicted in the graphical representation.

19. The method of claim 18, further comprising tracking the laparoscopic surgical instrument to provide data enabling the determination of the location, speed and direction data of the laparoscopic surgical instrument.

20. The method of claim 19, wherein the ultrasound image is registered with the location, speed and direction data.

* * * * *